United States Patent [19]

Nahmias et al.

[11] Patent Number: 5,691,155
[45] Date of Patent: Nov. 25, 1997

[54] NUCLEOTIDE SEQUENCES ENCODING THE MURINE β3-ADRENERGIC RECEPTOR AND THEIR APPLICATIONS

[75] Inventors: Clara Nahmias; Laurent Jean Emorine; Arthur Donny Strosberg, all of Paris, France

[73] Assignee: Centre National De La Recherche Scientifigue, Paris, France

[21] Appl. No.: 87,772

[22] PCT Filed: Jan. 14, 1992

[86] PCT No.: PCT/FR92/00023

§ 371 Date: Aug. 16, 1993

§ 102(e) Date: Aug. 16, 1993

[87] PCT Pub. No.: WO92/12246

PCT Pub. Date: Jul. 23, 1992

[30] Foreign Application Priority Data

Jan. 14, 1991 [FR] France .................. 91 00320

[51] Int. Cl.⁶ .................. C12N 15/12; C07K 14/435; C12Q 1/00
[52] U.S. Cl. .................. 435/7.21; 435/69.1; 435/252.3; 435/254.11; 435/320.1; 435/325; 530/300; 530/350; 536/23.5; 536/24.31
[58] Field of Search .................. 536/23.1, 23.5, 536/24.31; 530/350, 300; 435/69.1, 240.1, 240.2, 320.1, 7.21, 325, 252.3, 254.11

[56] References Cited

U.S. PATENT DOCUMENTS 5,053,337 10/1991 Weinshank et al. .................. 435/240.2

FOREIGN PATENT DOCUMENTS 351921  1/1990  European Pat. Off. .
WO 90/08775  8/1990  WIPO .

OTHER PUBLICATIONS

Cohen et al., Neurology, vol. 39 (Suppl. 1.), p. 388, 1989.

Baggott et al., Am. Rev. Respir. Dis., vol. 139, A366, 1989.

Lewin, Science, vol. 237, Sep. 25, 1987, p. 237.

Reeck et al., Cell, vol. 50, p. 667, 1987.

Nahmias, C. et al., "Molecular Characterization of the Mouse β3–Adrenergic Receptor: Relationship with the Atypical Receptor of Adipocytes", The EMBO Journal, vol. 10, No. 12, pp. 3721–3727, 1991.

Emorine, Laurent J. et al., "Molecular Characterization of the Human $β_3$–Adrenergic Receptor", Science, vol. 245, pp. 1118–1120, Sep. 8, 1989.

Emorine et al., Science, v. 245, p. 1118, 1989.

Primary Examiner—Stephen Walsh
Assistant Examiner—Sally P. Teng
Attorney, Agent, or Firm—Bell, Seltzer, Park & Gibson

[57] ABSTRACT

Nucleotide sequences encoding the murine β3-adrenergic receptor are provided. Use of the sequences as probes, in vectors, and for the expression of peptides are discussed. Methods of screening substances for agonist or antagonist action towards β3-adrenergic receptors, and for detecting the affinity of various substances for β3-adrenergic receptors, are described.

22 Claims, 13 Drawing Sheets

```
        10        20        30        40        50        60
ATGGCTCCGTGGCCTCAC-AGAAACGGCTCTCTGGCTTTGTGGTCGGACGCCCCTACCCTGGACCCCAGT
::::::::::::::::: ::::  ::::  ::::::::: ::  :::::: :::  :::::::: ::::
ATGGCTCCGTGGCCTCACGAGAA-CAGCTCTCTTGCCCCATGGCCGGACCTCCCCACCCTGGCGCCCAAT
640       650       660       670       680       690       700

80        90       100       110       120       130
GCAGCCAACACCAGTGGGTTGCCAGGAGTACCATGGGCAGCGGCATTGGCTGGGGCA-T--TG-C--TGG
 : ::::::::::::::::: ::::::: :: ::::: :::::: :: :: : ::::    ::    ::
ACCGCCAACACCAGTGGGCTGCCAGGGGTTCCGTGGGAGGCGGCCCTAGCCGGGGCCCTGCTGGCGCTGG
710       720       730       740       750       760       770

140       150       160       170       180       190       200
CG---CTGGCCACGGTGGGAGGCAACCTGCTGGTAATCATAGCCATCGCCCGCACGCCGAGACTACAGAC
::   ::::::::: ::::::::::::::::::: :::: :::::::::: ::: ::::::::: ::::
CGGTGCTGGCCACCGTGGGAGGCAACCTGCTGGTCATCGTGGCCATCGCCTGGACTCCGAGACTCCAGAC
780       790       800       810       820       830       840

210       220       230       240       250       260       270
CATAACCAACGTGTTCGTGACTTCACTGGCCGCAGCTGACTTGGTAGTGGGACTCCTCGTAATGCCACCA
::: ::::::::::::::::::::: ::::::::::: :::: ::: :::::::::: ::  :::: ::
CATGACCAACGTGTTCGTGACTTCGCTGGCCGCAGCCGACCTGGTGATGGGACTCCTGGTGGTGCCGCCG
850       860       870       880       890       900       910

280       290       300       310       320       330       340
GGGGCCACATTGGCGCTGACTGGCCATTGGCCCTTGGGCGAAACTGGTTGCGAACTGTGGACGTCAGTGG
  :::::: ::::::::::::::::: ::::: ::::::::  ::::  :: :::::::::  :: :::
GCGGCCACCTTGGCGCTGACTGGCCACTGGCCGTTGGGCGCCACTGGCTGCGAGCTGTGGACCTCGGTGG
920       930       940       950       960       970       980

350       360       370       380       390       400       410
ACGTGCTCTGTGTAACTGCTAGCATCGAGACCTTGTGCGCCCTGGCTGTGGACCGCTACCTAGCTGTCAC
::::::: ::::: ::  ::: :::::: : ::::::::::::::: :::::::::::::: :::: ::
ACGTGCTGTGTGTGACCGCCAGCATCGAAACCCTGTGCGCCCTGGCCGTGGACCGCTACCTGGCTGTGAC
990      1000      1010      1020      1030      1040      1050

420       430       440       450       460       460       480
CAACCCTTTGCGTTACGGCACGCTGGTTACCAAGCGCCGCGCCCGCGCGGCAGTTGTCCTGGTGTGGATC
::::::  :::::::::: :: :::::  ::::::::: ::::: ::  ::: :::::::::::: ::
CAACCCGCTGCGTTACGGCGCACTGGTCACCAAGCGCTGCGCCCGGACAGCTGTGGTCCTGGTGTGGGTC
1060      1070      1080      1090      1100      1110      1120

490       500       510       520       530       540       550
GTGTCCGCTGCCGTGTCCTTTGCGCCCATCATGAGCCAGTGGTGGCGTGTAGGGGCAGATGCCGAGGCAC
::::: ::::: ::::: :::::::::::::::::::::::::::::::::::::: :: :::::::: :
GTGTCGGCCGCGGTGTCGTTTGCGCCCATCATGAGCCAGTGGTGGCGCGTAGGGGCCGACGCCGAGGCGC
1130      1140      1150      1160      1170      1180      1190

560       570       580       590       600       610       620
AGGAATGCCACTCCAATCCGCGCTGCTGTTCCTTTGCCTCCAACATGCCCTATGCGCTGCTCTCCTCCTC
 : :::::::::::::::: ::::::::: :::: :::::::::::::::::: :::::::: ::::::
AGCGCTGCCACTCCAACCCGCGCTGCTGTGCCTTCGCCTCCAACATGCCCTACGTGCTGCTGTCCTCCTC
1200      1210      1220      1230      1240      1250      1260
```

FIG. 3A.

```
          630       640       650       660       670       680       690
CGTCTCCTTCTACCTTCCCCTCCTTGTGATGCTCTTCGTCTATGCTCGAGTGTTCGTTGTGGCTAAGCGC
:::::::::::::::::: ::  :: ::::::: :::::::: ::  ::  ::::  :::: ::::  ::::
CGTCTCCTTCTACCTTCCTCTTCTCGTGATGCTCTTCGTCTACGCGCGGGTTTTCGTGGTGGCTACGCGC
1270      1280      1290      1300      1310      1320      1330

700       710       720       730       740       750       760
CAACGGCATTTGCTGCGCCGGGAACTGGGCCGCTTCTCGCCCGAGGAGTCTCCGCCGTCTCCGTCGCGCT
::  :  :: :::::::::: ::::  ::::::::::  ::::::::::::::::::::  :::::::::
CAGCTGCGCTTGCTGCGCGGGGAGCTGGGCCGCTTTCCGCCCGAGGAGTCTCCGCCGGCGCCGTCGCGCT
1340      1350      1360      1370      1380      1390      1400

770       780       790       800       810       820       830
CTCCGTCCCCTGCCACAGGCGGGACACCCGCGGCACCGGATGGAGTGCCCCCCTGCGGCCGGCGGCCTGC
::: :  :::: ::: :: :::::::   :::: ::::: :::   :::::::::::::::::  :::::
CTCTGGCCCCGGCCCCGGTGGGGACGTGCGCTCCGCCCGAAGGGGTGCCCGCCTGCGGCCGGCGGCCCGC
1410      1420      1430      1440      1450      1460      1470

840       850       860       870       880       890       900
GCGCCTCCTGCCACTCCGGGAACACCGCGCCCTGCGCACCTTAGGTCTCATTATGGGCATCTTCTCTCTG
::::::::::: ::::::::::::::: :::::::: ::::::::::::::: ::::::: :: :: :::
GCGCCTCCTGCCTCTCCGGGAACACCGGGCCCTGTGCACCTTGGGTCTCATCATGGGCACCTTCACTCTC
1480      1490      1500      1510      1520      1530      1540

910       920       930       940       950       960       970
TGCTGGCTGCCCTTCTTCCTGGCCAACGTGCTGCGCGCACTCGCGGGGCCCTCTCTAGTTCCCAGCGGAG
::::::  :::::::::: :::::::::::::::: ::: :: :::::::: ::::::: ::: ::  :
TGCTGGTTGCCCTTCTTTCTGGCCAACGTGCTGCGCGCCCTGGGGGGCCCCTCTCTAGTCCCGGGCCCGG
1550      1560      1570      1580      1590      1600      1610

980       990       1000      1010      1020      1030      1040
TTTTCATCGCCCTGAACTGGCTGGGCTATGCCAACTCCGCCTTCAACCCGGTCATCTACTGCCGCAGCCC
 ::::  ::::::::::::::::    ::::::: ::::::::::::::::  :::::::::::::::::
CTTTCTTTGCCCTGAACTGGCTAGGTTATGCCAATTCTGCCTTCAACCCGCTCATCTACTGCCGCAGCCC
1620      1630      1640      1650      1660      1670      1680

1050      1060      1070      1080      1090      1100      1110
GGACTTTCGCGACGCCTTCCGTCGTCTTCTGTGTAGCTACGGTGGCCGTGGACCGGAGGAGCCACGCGCA
:::::::::::  :::::::::: ::::::::::  :: :: :::::: :::   :: ::::: ::::::
GGACTTTCGCAGCGCCTTCCGCCGTCTTCTGTGCCGCTGCGGCCGTCGCCTGCCTCCGGAGCCCTGCGCC
1690      1700      1710      1720      1730      1740      1750

1120
GTCACCTTCCCAGCC
:::  ::   :::::
GCCGCCCGCCCGGCC
1760      1770
```

FIG. 3B.

```
                                        tm1
       10       20        30       40         50        60
MAPVPHRNGSLALVSDAPTLDPSAANTSGLPGVPW AAALAGALLALA---TVGGNLLVTIAIAR
====== =-===  = = === = -=========== ==========  ==========-===
MAPVPHENSSLAPVPDLPTLAPNTANTSGLPGVPW EAALAGALLALAVLATVGGNLLVIVAIAW
       10       20       30       40        50        60
                    tm2                              tm3
        70        80       90       100      110       120
TPRLQTII NVFVTSLAAADLVVGLLVMPPGSTLSLT GHVPLGETGCEL VTSVDVLCVTASIET
======== =======================-==== ==-========= ===============
TPRLQTMT NVFVTSLAAADLVMGLLVVPPASTLALT GHVPLGATGCEL VTSVDVLCVTASIET
        70        80       90       100      110       120
                                            tm4
       130      140      150      160       170      180
LCALA VDRYLAVTNPLRYGTLVTKRRAR AAVVLVVIVSAAVSFAPIMSQVV RVGADAEAQECH
===== =============-===== ==-======------============ =========== ==
LCALA VDRYLAVTNPLRYGALVTKRCAR TAVVLVVVVSAAVSFAPIMSQVV RVGADAEAQRCH
 130      140      150       160       170      180       190
                    tm5
       190       200      210      220      230      240      250
SNPRCCSFASNMP YALLSSSVSFYLPLLVMLFVYA RVFVVAKRQRHLLRRELGRFSPEESPPS
============= ======================= ===== === ===== ======-
SNPRCCAFASNMP YVLLSSSVSFYLPLLVMLFVYA RVFVVATRQLRLLRGELGRFPPEESPPA
       200       210      220      230      240      250
                                                         tm6
        260      270      280      290       300      310
PSRSPSPATGGTPAAPDGVPPCGRRPARLLPLREHRALR TLGLIMGIFSLCVLPFFLANVL RA
==== -== == = =-=== ================= ======= =-============== ==
PSRSLAPAPVGTCAPPEGVPACGRRPARLLPLREHRALC TLGLIMGTFTLCVLPFFLANVL RA
        260      270      280      290       300      310
                     tm7
         320      330      340      350      360      370
LAGPSLVPSG VFIALNWLGYANSAFNPVIYQ RSPDFRDAFRRLLCSYGGRGPEEP----RAVTF
=-======- ==================-== ========  = = == =      = =
LGGPSLVPPP AFLALNWLGYANSAFNPLIYQ RSPDFRSAFRRLLCRCGRRLPPEPCAAARPALF
         320      330      340      350      360      370      380
   380
PASPVEARQSPPLNR
===   == ==  =
PSGVPAARSSPAQPRLCQRLDG
     390      400
```

NUCLEOTIDE SEQUENCES ENCODING THE MURINE β3-ADRENERGIC RECEPTOR AND THEIR APPLICATIONS

This application is a national phase application under 35 U.S.C. §371 of PCT application PCT/FR92/00023, filed Jan. 14, 1992.

The present invention relates to nucleotide sequences encoding the murine β3-adrenergic receptor (RAβ3), to the use of the said sequences as probes and for the expression of peptides and/or fragments thereof which have a murine RAβ3 activity, to vectors useful for the said expression as well as to host cells containing the said vector.

The present invention also relates to polyclonal and monoclonal antibodies directed against the said peptides and which can be used especially for the detection of murine β3-adrenergic receptors as well as to a process for screening substances with agonist or antagonist action towards peptides having a β3-adrenergic receptor action, and to boxes or kits for the detection of the degree of affinity of various substances for the said peptides with β3-adrenergic receptor activity. Such substances can especially be used as medicinal and products in the treatment of obesity, diabetes mellitus and diabetes of non-insulin-dependent subjects as well as in the treatment of hyperlipidemias.

BACKGROUND OF THE INVENTION

It is known that catecholamines such as adrenaline and noradrenaline, synthetic agonists of these catecholamines which mimic their biological functions, and antagonists which block these biological functions, exert their effects by binding to specific recognition sites (membrane receptors) situated on the cell membranes.

Two principal classes of adrenergic receptors have been defined, the α-adrenergic receptors and the β-adrenergic receptors.

In both of these two classes, five subtypes of catecholamine receptors (α1, α2, β1, β2 and β3-RA) can now be distinguished. Their genes were recently isolated and identified (S. COTECCHIA et al., 1988, Proc. Natl. Acad. Sci. USA, 85, 7159–7163; B. K. KOBILKA et al., 1987, Science, 238, 650–656; T. FRIELLE et al., 1987, Proc. Natl. Acad. Sci. USA 84, 7920–7924; L. J. EMORINE et al., 1987, Proc. Natl. Acad. Sci., USA, 84, 6995–6999; L. J. EMORINE et al., 1989, Science, 245, 1118–1121). Analysis of these genes has made it possible to recognise that they belong to a family of integral membrane receptors exhibiting some homology (R. A. F. DIXON et al., 1998, Annual Reports in Medicinal Chemistry, 221–223; L. J. Emorine et al., 1988, Proc. NATO Adv. Res. Workshop), especially at the level of 7 transmembrane regions which are coupled to regulatory proteins, called G proteins, capable of binding molecules of guanosine triphosphate (GTP).

These membrane receptors, after they have bound the appropriate ligand (agonist or antagonist), undergo a conformational change which induces an intracellular signal which modifies the behavior of the target cell. In the case of β-adrenergic receptors, when they bind with agonists of catecholamines, they catalyse the activation of a class of G proteins which in turn stimulates the activity of adenylate cyclase whereas the antagonists of RAβ receptors act in competition with the agonists for the binding to the receptor and prevent the activation of adenylate cyclase.

When adenylate cyclase is activated, it catalyses the production of an intracellular mediator or second messenger, especially cyclic AMP.

SUMMARY OF THE INVENTION

A first aspect of the present invention is an isolated DNA molecule having the nucleotide sequence of SEQ ID NO:1 and encoding the murine β3-adrenergic receptor protein.

A further aspect of the present invention is an isolated DNA molecule having the nucleotide sequence of SEQ ID NO:3.

A further aspect of the present invention is an isolated DNA molecule having the nucleotide sequence of SEQ ID NO:4, which sequence includes the coding region of the murine β3-adrenergic receptor protein gene.

A further aspect of the present invention is an isolated DNA molecule of SEQ ID NO:6.

A further aspect of the present invention is an isolated DNA molecule of SEQ ID NO:7.

Another aspect of the present invention is a nucleotide probe having a sequence of SEQ ID NO:1, SEQ ID NO:3, SEQ ID NO:4, SEQ ID NO:6 or SEQ ID NO:7.

Another aspect of the present invention is a polypeptide having β-adrenergic receptor activity and having the amino acid sequence of SEQ ID NO:2.

A further aspect of the present invention is an expression vector containing the nucleotide sequence of SEQ ID NO:1.

Another aspect of the present invention is the vector deposited as I-1026 with the Collection Nationale de Cultures de Microorganisms, Institut Pasteur.

A further aspect of the present invention is a method of assaying a substance for agonist activity towards a polypeptide having SEQ ID NO:2. In this method a transformed host cell expressing the murine β3 adrenergic receptor polypeptide encoded by SEQ ID NO:1, SEQ ID NO:3 or SEQ ID NO:4 is placed in contact with the substance being tested, and cAMP production is measured. A further aspect of the present invention is a process for studying the binding affinity of a compound for a polypeptide of SEQ ID NO:2, wherein a host cell expressing a β3 receptor protein is placed in contact with the test compound and the amount of compound which binds to the β3 receptor protein is measured.

Another aspect of the present invention is a kit for assaying the binding affinity of a compound for the murine β3-adrenergic receptor encoded by SEQ ID-NO:1, SEQ ID NO:3 or SEQ ID NO:4.

A further aspect of the present invention is antibodies directed against a polypeptide of SEQ ID NO:2.

BRIEF DESCRIPTION OF THE DRAWINGS

FIG. 3A compares the encoding regions of the murine (top lines; SEQ ID NO:3) and human (bottom lines; SEQ ID NO:14) β3 adrenergic receptor genes.

FIG. 3B continues the comparison of FIG. 3A, between the encoding regions of the murine (top lines; SEQ ID NO:3) and human (bottom lines; SEQ ID NO:14) β3 adrenergic receptor genes.

FIG. 4 compares the amino acid sequences of the murine (top lines; SEQ ID NO:2) and human (bottom lines; SEQ ID NO:15) β3 adrenergic receptors.

FIG. 5A compares the amino acid sequences of the human β3 (β3-AR; SEQ ID NO:15), β1 (β1-AR; SEQ ID NO:16) and β2 (β2-AR; SEQ ID NO:17) adrenergic receptors with the murine β3 (Mβ3-AR; SEQ ID NO:2) adrenergic receptor.

FIG. 5B is a continuation of the comparison of FIG. 5A.

DETAILED DESCRIPTION

Figure 1:
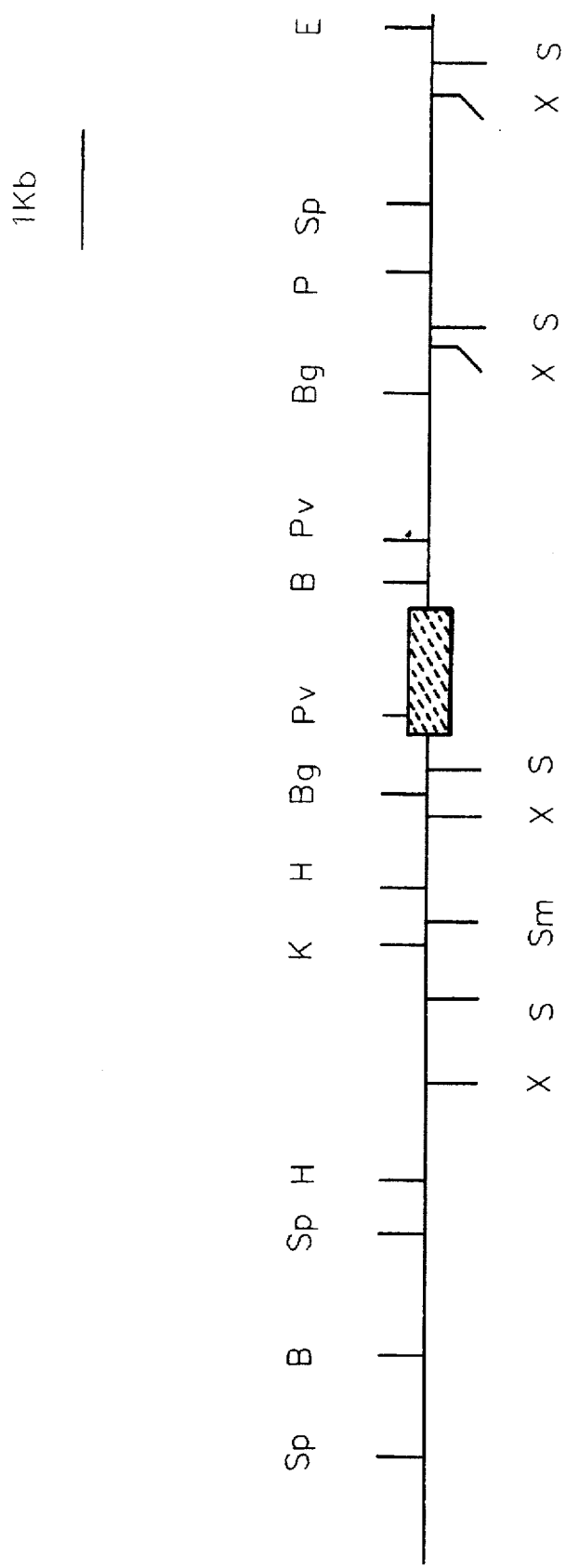
FIG. 1 provides the restriction map of the clone MB1 which contains the murine β3-adrenergic receptor gene and comprises 14 Kb.

The Inventors recently identified new β-adrenergic receptors in man, called RA-Huβ3 and characterised by properties different from those of the β1 and β2 receptors especially in that they behave differently towards substances which are respectively antagonists and agonists of the β1 and β2 receptors (French Patent Application No. 89 00918).

Such an RA-Huβ3 receptor more particularly consists of a sequence of 402 amino acids and is considered as also comprising seven hydrophobic transmembrane regions separated by hydrophilic intra- and extra-cellular loops.

Pursuing their work in this direction, the present inventors sought to identify such an RAβ3 in rodents and more particularly in murines in order to be able to have especially a model for studying β-adrenergic ligands.

The subject of the present invention is a nucleic acid sequence, characterised in that it comprises the murine gene which encodes a peptide having a β3-adrenergic receptor activity, that is to say that it is capable of participating in the activation of adenylate cyclase in the presence of at least one of the following agonists: BRL 28410, BRL 37344, CGP 12177A and (1)-isoproterenol.

The agonist CGP 12177A is especially described in the article in the name of N. MOHELL et al. (Biochem. J., 1989, 261, 401–405) and the agonists BRL 28410 and BRL 37344 are described in the article in the name of J. R. S. ARCH et al. (Nature, 1984, 309, 5964, 163–165).

According to an advantageous embodiment of the said sequence, it contains 1920 base pairs and comprises the nucleotide sequence (SEQ ID NO:1) as well as sequences derived therefrom and fragments of the said sequence and derived sequences.

The said sequence comprises especially the following unique restriction sites:
AlwN I, Sac I, Stu I, Dra I, Mse I, Bbe I, Nar I, Xcm I, NCo I, BspM I, Afl III, Pvu I, Nhe I, BstE II, BspH I, Bsm I, Nsp7524 I, NspH I, Xho I, Sac II, Eag I, Nae I, PaeR7 I, EcoN I, Fsp I, Bbv II, Nru I, Drd I, BamH I.

The subject of the invention is also fragments of the said sequence which are useful for the expression of the corresponding peptide and/or the detection of the murine gene which encodes the murine β3 receptor.

Amongst the said fragments, the sequence comprises inter alia:

a sequence consisting of a segment of 1164 nucleotide (SEQ ID NO:3) which corresponds to nucleotides 568–1731 of (SEQ ID NO:1), a sequence consisting of a segment of 1360 base pairs (SEQ ID NO:4) containing the coding region of the murine β3 gene and a portion of the untranslated 3' region which corresponds to nucleotides 555–1914 of SEQ ID NO:1, a sequence consisting of a segment of 281 nucleotide base pairs (SEQ ID NO:5) which corresponds to nucleotides 1640–1920 of (SEQ ID NO:1), a sequence consisting of a segment of 609 nucleotide base pairs (SEQ ID NO:6) situated between the transmembrane regions TM3 and TM6 and which corresponds to nucleotides 895–1503 of (SEQ ID NO:1), a sequence consisting of a segment of 298 nucleotide base pairs (SEQ ID NO:7) going from the translational initiation codon up to the end of the TM2 domain and which corresponds to nucleotides 567–864 (region of the gene which encodes the amino-terminal portion of the peptide) of (SEQ ID NO:1).

Nucleic acids which are variants relative to those defined above and which contain certain localised mutations also form part of the invention insofar as these variant nucleic acids hybridize with the nucleic acids defined above and with fragments thereof.

Within the context of the present invention, derived sequence is understood to mean both a single-stranded or double-stranded DNA or RNA sequence and their complementary sequences.

The subject of the present invention is also nucleotide probes, characterised in that they hybridize with the nucleotide sequences as defined above but do not hybridize with the genes which encode the β1- and β2-adrenergic receptors, nor with the messenger RNA of the said β1- and β2-adrenergic receptors, and in that they are optionally labelled by means of a marker such as a radioactive isotope, an appropriate enzyme or any other appropriate non-radioactive substance.

According to an advantageous embodiment of the said probe, its sequence is homologous or complementary to that of a segment of at least 10 bp of (SEQ ID NO:1).

Within the context of the present invention, "homologous sequence" comprises not only sequences identical to (SEQ ID NO:1), or to a fragment thereof, but also those differing from it by only a substitution, deletion or addition of a small number of nucleotides, provided that the sequences thus modified have a hybridization specificity equivalent to that of (SEQ ID NO:1) or the segment considered.

Likewise, "complementary sequence" is understood to mean not only sequences strictly complementary to (SEQ ID NO:1) or to its segments, but also modified sequences, as indicated above, possessing a hybridization specificity equivalent to that of the said strictly complementary sequences.

The hybridization conditions are defined as follows:

For the shortest probes, that is to say of about 10 to about 100 nucleotides, appropriate hybridisation conditions are the following:

750 mM of NaCl, 75 mM of trisodium citrate, 50 µg/ml of salmon sperm DNA, 50 mM of sodium phosphate, 1 mM of sodium pyrophosphate, 100 µM of ATP, 10 to 25% formamide, 1% Ficoll ("PHARMACIA" average molecular weight of 400,000), 1% polyvinylpyrrolidone, 1% bovine serum albumin, for 14 to 16 h at 42° C.

For the longest probes, that is to say having more than about 100 nucleotides, appropriate hybridization conditions are those indicated above for the shortest probes, but in which the above defined medium contains 40% formamide instead of 10 to 25% formamide.

According to an advantageous form of this embodiment, the said probe may be advantageously defined by any of the nucleotide sequences defined above and especially:

the fragment of 1920 base pairs, which corresponds to the entire sequence of (SEQ ID NO:1);

the fragment of about 600 bp, (SEQ ID NO:6) which corresponds to the fragment situated between the transmembrane regions TM3 and TM6 of the sequence of (SEQ ID NO:1) above;

the fragment of about 300 bp, (SEQ ID NO:7) which corresponds to the region of the gene which encodes the amino-terminal portion of the peptide going from the translational initiation codon up to the end of the TM2 domain;

the fragment of about 280 base pairs, (SEQ ID NO:5) which corresponds to segment 1640–1920 of (SEQ ID NO:1).

Such probes have especially the advantage of allowing the characterisation of genetically defined inbred lines of diabetic and/or obese mice, especially db/db, ob/ob, NOD lines.

The subject of the present invention is also a peptide and/or a peptide fragment, characterised in that it is encoded by a nucleotide sequence as defined above and in that it exhibits a β3-adrenergic receptor activity.

A β3-adrenergic receptor activity is that defined in French Patent Application No. 89 00918, namely that when the fragment is exposed at the surface of a cell, it is capable of participating in the activation of adenylate cyclase in the presence of one of the following agonists: BRL 28410, BRL 37344, CGP 12177A and (1)-isoproterenol; either it is capable of being recognised by antibodies which recognise neither the β1-adrenergic receptor nor the β2-adrenergic receptor, or it is capable of generating antibodies which recognise neither the β1 receptor nor the β2 receptor.

According to an advantageous embodiment of the said peptide, it comprises 388 amino acids and has the amino acid sequence (SEQ ID NO:2), which peptide has 82% homology with the human β3 peptide (human β3 receptor).

This peptide is called hereinafter murine β3-adrenergic receptor (RA-Muβ3).

It was not clear whether murines possess a β3-adrenergic receptor and whether the latter is furthermore sufficiently homologous to the human β3-adrenergic receptor to permit its use as a general model for studying the β3-adrenergic receptor.

The murine RA-β3 (RA-Muβ3) has indeed a certain number of advantages:

it is particularly suitable as model of the β3-adrenergic receptor, in particular for physiological studies which cannot be performed with the human receptor;

it makes it possible to study the regulation of the expression of the β3-adrenergic receptor under various physiological conditions (exposure to cold or to β-adrenergic ligands) which may modify the lipolytic and/or thermogenic activity since the β3-adrenergic receptor is involved in diseases such as diabetes and/or obesity insofar as it is expressed in tissues which play an important part in metabolism (adipose tissues, skeletal muscle in particular);

it makes it possible, in addition, to analyse the expression of the β3-adrenergic receptor during the embryonic development.

The invention also comprises the variant peptides of those defined above, which contain certain mutations without the peptides losing the β3-adrenergic receptor properties. Among these variants, there may be mentioned those which are recognised by antibodies recognising the transmembrane regions, as well as those which are recognised by antibodies recognising regions other than the transmembrane regions.

The subject of the present invention is also fragments or combinations of fragments of RA-muβ3 conforming to the invention, and especially:

a fragment of 25 amino acids (SEQ ID NO:8), corresponding to the transmembrane region TMI of (SEQ ID NO:2);

a fragment of 30 amino acids (SEQ ID NO:9), corresponding to the COOH-terminal fragment of (SEQ ID NO:2).

The said fragments are advantageously obtained by synthesis, especially by the Merrifield method.

The subject of the present invention is also a recombinant cloning and/or expression vector, characterised in that it comprises a nucleotide sequence conforming to the invention.

Within the context of the present invention, recombinant vector is understood to mean at the same time a plasmid, a cosmid and a phage.

According to an advantageous embodiment of the said vector, it consists of an appropriate recombinant vector comprising in particular a replication origin in an appropriate host microorganism, especially a bacterium or a eukaryotic cell, at least one gene whose expression allows the selection either of bacteria or of eukaryotic cells which have received the said vector, an appropriate regulatory sequence, especially a promoter which permits the expression of genes in the said bacteria or eukaryotic cells, and in which is inserted a nucleotide sequence or a fragment of sequence as defined above, which vector is a vector for the expression of a peptide, a peptide fragment or a combination of peptide fragments having a murine β3-adrenergic receptor activity.

According to an advantageous form of this embodiment, the said expression vector successively consists of an appropriate replication origin, a gene for resistance to ampicillin, the viral promoter SV40, a nucleotide sequence conforming to the invention which encodes a peptide having a murine β3-adrenergic receptor activity, a polyadenylation site derived from the hepatitis B virus (HBsAg) and the gene which encodes the dihydrofolate reductase (DHFR), which enzyme permits the survival of cells in a medium lacking glycine, hypoxanthine and thymidine.

Such a plasmid was called pSTH-Moβ3 by the Inventors and was deposited under the number I-1026 on 14 Jan. 1991 with the Collection Nationale de Cultures de Microorganismes held by INSTITUT PASTEUR.

The subject of the present invention is also an appropriate host cell, obtained by genetic transformation, characterised in that it is transformed by an expression vector conforming to the invention.

Such a cell is capable of expressing a peptide of murine origin which has a β3-adrenergic receptor activity.

According to an advantageous embodiment, the host cell especially consists of cells of the CHO line (Chinese Hamster Ovary).

Another of the microorganisms used may consist of a bacterium, especially *Escherichia coli*.

The subject of the present invention is also a method of expression of a peptide conforming to the invention, characterised in that the host cell, resulting from transformation by a vector containing a nucleotide sequence or a fragment thereof, which encodes a peptide of murine origin having a β3-adrenergic receptor activity or a fragment thereof, is cultured so as to produce and transport the said expressed peptide to the membrane, such that the transmembrane sequences of the said β3 receptor are exposed at the surface of the membrane of the transformed host cell.

In the case of expression in eukaryotic cells, the regulatory elements may comprise the endogenous promoter for the adrenergic receptors or viral promoters such as those of SV40 viruses or of the Rous sarcoma virus (RSV).

In the case of expression in *E. coli*, the regulatory elements may comprise the lactose operon or tryptophan operon promoter.

The subject of the present invention is also a model for studying the β3-adrenergic receptors, characterised in that it consists of host cells conforming to the invention, that is to say expressing a murine β3-adrenergic receptor at the surface of their cell membrane.

Such a model makes it possible to study, from a pharmacological point of view, murine β3-adrenergic receptors, especially by permitting the identification of β-adrenergic ligands with greater affinity for the β3-adrenergic receptor or more selective with respect to the β1 and β2 receptors and thereby the development of active medicinal products for diseases such as diabetes and/or obesity.

The subject of the invention is also a process for detecting the capacity of a substance to behave like a ligand towards a peptide conforming to the invention, which process comprises:

the placing of the said substance in contact with a host cell previously transformed with an expression vector conforming to the invention, which host cell expresses the said murine peptide (murine RAβ3), where appropriate after suitable physical or chemical induction, and which placing in contact is carried out under conditions which permit the formation of a bond between at least one of the specific sites and the said substance if appropriate; and the detection of the possible formation of a ligand-peptide type complex.

The subject of the present invention is furthermore a method of producing transgenic mice over-expressing the β3-adrenergic receptor, which method comprises the introduction of several copies of a segment comprising at least the sequence of formula I combined with a suitable promoter, into the cells of a mouse embryo at an early stage.

According to an advantageous embodiment of the said method, the promoter is the promoter of the RA-Muβ3 gene, especially so as to take into account its original distribution in tissue.

According to another advantageous embodiment of the said method, the promoter is a promoter of a gene specifically expressed in a tissue, especially the promoter for muscle actin.

The subject of the present invention is furthermore transgenic mice, characterised in that they are obtained by the method of producing transgenic mice as defined above.

The subject of the present invention is also a method of producing recombinant mice no longer expressing the β3-adrenergic receptor, characterised in that:

a suitable mutation is produced in the sequence of (SEQ ID NO:1) conforming to the invention which inhibits the expression of the gene which encodes the murine β3-adrenergic receptor;

the said modified (SEQ ID NO:1) is introduced into a segment of mouse genomic DNA, combined with an appropriate marker, so as to obtain a labelled sequence M containing the modified sequence of (SEQ ID NO:1);

the said sequence M is integrated in vitro into the stem cells of mouse embryo germ lines; then the said stem cells are reinjected into a mouse; and after homologous recombination, homozygous recombinant mice are obtained at the F2 generation which are recognisable by the presence of the marker.

A procedure for recombinant mice is for example described in Nature, 1988, 336, 348–352.

According to an advantageous embodiment of the said method, the said segment of mouse genomic DNA comprises at most 14 Kbases.

According to an advantageous form of this embodiment, when the said fragment is 14 Kbases, it comprises especially the following restriction sites: 3 SphI sites, 2 BamHI sites, 2 HindIII sites, 4 XbaI sites, 4 SacI sites, 1 KpnI site, 1 SmaI site, 2 BglII sites, 2 PvuII sites, 1 PstI site and 1 EcoRI site.

According to another advantageous embodiment of the said method, the mutated (SEQ ID NO:1) is between a BglII site and a BamHI site of the segment of mouse genomic DNA.

The subject of the present invention is furthermore recombinant mice, characterised in that they are obtained by the method of producing recombinant mice as defined above.

The transgenic mice and the recombinant mice as defined above are a particularly advantageous model, from a physiological point of view, for studying β3-adrenergic receptors.

The subject of the present invention is in addition a process for studying the affinity of a polypeptide conforming to the invention for one or more determined ligands, which process comprises:

the transformation of an appropriate host cell by an expression vector conforming to the invention;

the culture of the transformed host cell under conditions which permit the expression of the β3 receptor encoded by the nucleotide sequence, and the transfer of the expressed β3 receptor to the membrane of the said cell so that the transmembrane sequences of the β3 receptor are exposed at the surface of the transformed host cell;

the placing of the said cell in contact with the determined ligands; and the detection of an affinity reaction between the said transformed cell and the said determined ligands.

The subject of the invention is in addition a kit for detecting the affinity, where appropriate, of a ligand for a peptide conforming to the invention, which kit comprises:

a culture of host cells transformed by an expression vector conforming to the invention;

optionally, if necessary, physical or chemical means for inducing the expression of a peptide (murine β3 receptor or a fragment thereof) encoded by a nucleotide sequence conforming to the invention which is contained in a vector whose promoter is inducible;

one or more control ligands having determined affinities for the said peptide; and physical or chemical means for characterising the biological activity of the peptide expressed.

The subject of the invention is also antibodies directed specifically against one of the peptides conforming to the invention, these antibodies being such that they recognise neither the β1-adrenergic receptor nor the β2-adrenergic receptor.

According to an advantageous embodiment, the said antibodies are polyclonal antibodies.

According to an advantageous embodiment, the said antibodies are monoclonal antibodies.

The monoclonal antibodies are prepared by cell fusion between myeloma cells and spleen cells of immunised mice according to conventional processes.

Surprisingly, the murine β3-adrenergic receptor permits the implementation of all the abovementioned applications.

In addition to the forms above, the invention also comprises other forms which will become apparent from the description below which refers to exemplary embodiments of the process which is the subject of the present invention.

It should be clearly understood however that these examples are given solely as illustration of the subject of the invention and do not constitute in any manner a limitation thereof.

EXAMPLE 1

Isolation and Identification of the Murine β3-Adrenergic Gene

The murine β3 gene was isolated from a mouse genomic DNA library of the NIH-3T3 line constructed in the phage λ-FixII, using as probe a 1034-bp DNA fragment (Huβ3 probe) containing the entire human β3-adrenergic gene previously isolated (EMORINE. et al., Science, 245, 1118–1121, 1989). After hybridization with the radio labelled probe, the filters are washed and exposed overnight on autoradiographic film. 24 hybridization signals were observed of which 18 subsequently proved to be false positives. The remaining 6 clones (MB1, MB2, MB3, MB4, MB9, MB12) were purified by 4 successive subclonings followed by a hybridization with the probe Huβ3 (see French Application 89 00918).

In order to identify the clone(s) containing the murine β3-adrenergic gene, two methods were used: hybridization with other β-adrenergic probes, and PCR amplification. DNA was prepared from the 6 clones, cut with restriction endonucleases and then hybridized with several probes derived from β-adrenergic genes, as shown in Table I below.

TABLE I

|  | PROBES | | | | | |
| --- | --- | --- | --- | --- | --- | --- |
|  | Huβ3 | Huβ1 | Huβ2 | i3β3 | 3'β1 | i3β2 |
| Gene |  |  |  |  |  |  |
| Human β1 | ++ | +++ | ++ | − | + | − |
| Human β2 | + | ++ | +++ | − | − | − |
| Human β3 | +++ | ++ | + | + | − | − |
| Clone |  |  |  |  |  |  |
| MB1 | +++ | + | − | + | − | − |
| MB2 | +++ | + | − | + | − | − |
| MB3 | +++ | + | − | + | − | − |
| MB4 | +++ | + | − | + | − | − |
| MB9 | +++ | + | − | + | − | − |
| MB12 | + | − | − | − | − | − |

The probes used are all derived from the human β-adrenergic genes, β1, β2 or β3, as described in French Patent Application No. 89 00918.

Probes Huβ1, Huβ2 and Huβ3 (about 1.2 Kb) respectively contain the entire coding regions of the β1, β2 and β3 genes. As indicated at the top of Table I, each of the probes hybridises with three human genes.

Probes 3'β1, i3β2 and i3β3 (about 200 to 300 bp) correspond to the carboxy-terminal part of β1AR, and to the third intracellular loop of β2AR and β3AR, respectively. These probes are derived from regions which are highly divergent between the β1, β2 and β3 genes, and are therefore specific: as indicated by the upper part of Table I, each of the probes hybridize only with the corresponding gene.

It is evident from the above that the clones MB1, MB2, MB3, MB4 and MB9 hybridize very strongly with the probe Huβ3, and also hybridize with the probe i3β3. The clone MB12 hybridizes very weakly with the starting probe Huβ3, and not at all with the specific probe i3β3. Moreover, comparison of the profiles for the digestion of these six clones with several restriction enzymes shows that MB1, MB4, MB9 on the one hand, and MB2, MB3 on the other hand, are identical, and that these two groups of clones overlap. Clones MB1, MB4 and MB9 are the most useful because the region which hybridizes with the probe is situated roughly in the middle of the cloned DNA fragment.

In order to show that MB1 indeed contains the murine β3-adrenergic gene, PCR amplification experiments were carried out using as primers either "degenerate" oligonucleotides situated in the most conserved domains between the various β-adrenergic genes, or "specific" oligonucleotides of the human β3-adrenergic gene, derived from the most divergent sequences between the three genes. In both cases, an amplification product of the expected size was able to be obtained using the MB1 clone DNA as template.

From these two hybridization and amplification experiments, it was possible to deduce that the clones of the MB1 family contain the murine β3-adrenergic gene.

EXAMPLE 2

Location of the β3-Adrenergic Gene in the MB1 Clone

The DNA of the MB1 clone, which comprises 14 Kb, was digested with twelve restriction enzymes, either separately or in pairs. The resulting fragments were deposited onto agarose gel, transferred onto nylon membrane and hybridized with the Huβ3 probe. After washing and exposure on autoradiographic film, the fragments hybridizing with the probe were able to be identified and the restriction map of the MB1 clone was established (FIG. 1).

In the case of the use of a single restriction enzyme, there is obtained a fragment of 3.6 kb with BglII, of 13 kb with PstI, of 4.1 kb with SacI and of 6.9 kb with BamHI.

The smallest DNA fragment hybridizing with the Huβ3 probe is a fragment of about 1.7 Kb flanked by the SacI and BamHI sites. It is therefore in this fragment that the murine β3-adrenergic gene is located.

EXAMPLE 3

Sequencing of the Murine β3-Adrenergic Gene

The DNA fragment of about 2 Kb, flanked by the sites of the enzymes BglII and BamHI was (SEQ ID NO:1) (see FIG. 1).

This DNA fragment was purified from the DNA of the MB1 clone and subcloned into the BamHI site of vector M13mp18. The M13 clones having integrated the DNA fragment in the two opposite orientations were identified (MB1BB1 and MB1BB2 clones). The DNA of these two M13 clones was prepared and deleted with exonuclease III (ExoIII). Several deletants were isolated, their single-stranded DNA was prepared and sequenced by the Sanger method.

Figure 2:
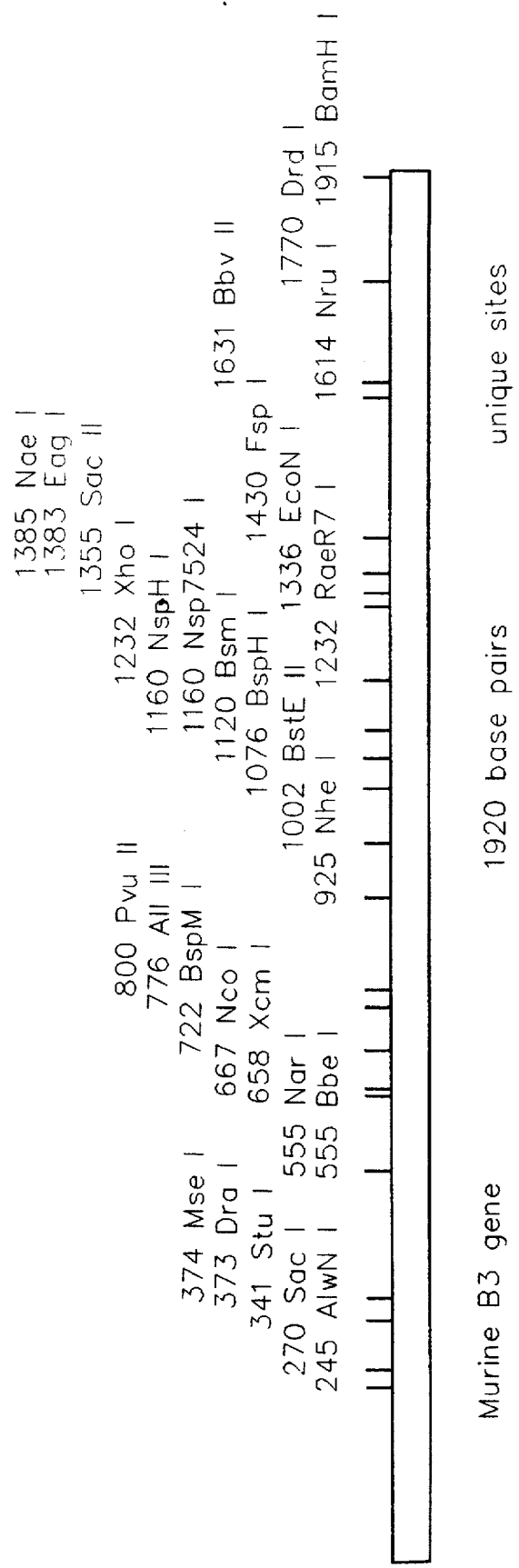
FIG. 2 provides the unique restriction sites of the sequence of SEQ ID NO:1 (the murine β3 adrenergic receptor gene).

The nucleotide sequence of the mouse β3 gene (1180 bp) and of the noncoding regions (555 bp in 5' and 186 bp in 3' of the gene) is represented by (SEQ ID NO:1). The positions of the restriction sites contained in this 1920-bp fragment are indicated in FIG. 2.

Comparison of the coding regions of the human and murine β3 genes indicates an 82% nucleotide conservation (FIG. 3) whereas they exhibit a homology of the order of only 48–55% with the RA-β1 and β2 genes of the various species. The murine β3 gene does not contain any intron and encodes a polypeptide of 388 amino acids which exhibits 82% homology with the human β3 polypeptide (FIG. 4). This homology is mainly concentrated in the transmembrane regions (93%) ("TM").

EXAMPLE 4

Preparation of Probes Specific for the Murine β3-Adrenergic Gene

Three DNA fragments were purified with the aim of obtaining a probe specific for the murine β3 gene.

The probe "A19" corresponds to the 2-Kb BglII-BamHI fragment which was sequenced (SEQ ID NO:7). This fragment was purified by running on agarose gel, electroeluting and passing through an ion-exchange column (NACS).

The probe "A20" corresponds to the amplification product obtained by PCR from the murine β3 gene using as primers the "degenerate" oligonucleotides (5'-AAGCTTGT/CGTG/CACG/CGCCAGCATC/TGAG/AACCCTGTG-3' (SEQ ID NO:10), and 5'-GTCGACAAGAAGGGCAGC/ACAGCAGAGG/C/AGTGAA-3' (SEQ ID NO:11) in a reaction medium comprising: 100 mM Tris-HCl pH 8.4, 30 mM MgCl$_2$, 0.5% Tween 20, 0.25% Nonidet P40, 5% formamide and 10% dimethyl sulphoxide. The DNA fragment obtained (about 600 bp) comprises the portion of the gene contained between the transmembrane regions TM3 and TM6 (SEQ ID NO:6). After amplification, the ends of the A20 fragment were filled with polymerase I "Klenow" fragment. The probe was then purified by running on polyacrylamide gel, electroeluting and passing through an ion-exchange column.

The "A21" probe corresponds to the amplification product obtained by PCR from the murine β3 gene using as primers oligonucleotides "specific" for the human β3 gene (5'-GCATGCTCCGTGGCCTCACGAGAA-3' (SEQ ID NO:12) and 5'-CTGCAGGAGGAGGACAGCAGCA-3') (SEQ ID NO:13) in a reaction medium comprising 670 mM Tris-Hcl pH 8.4, 67 mM MgCl$_2$, 1 mg/ml gelatin, 67 µM EDTA, 100 mM β-mercaptoethanol, 160 mM (NH$_4$)$_2$SO$_4$, 5% formamide and 10% dimethyl sulphoxide. The DNA fragment obtained (about 300 bp) comprises the amino-terminal region of the gene, going from the translational initiation codon up to the end of the TM2 domain (SEQ ID NO:7). The A21 probe was purified in the same manner as the A20 probe.

Figure 6A:
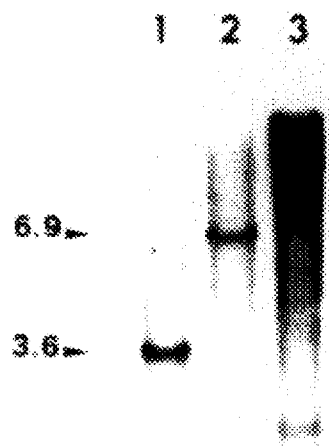
FIG. 6 presents the detection, by autoradiography (Southern blotting), of genomic DNA which hybridizes with probes specific for the β3-adrenergic gene. Lanes 1 and 2 contain genomic DNA from mouse livers and lanes 3 contain genomic DNA from human cells. The DNA was probed with radiolabelled probe A19 (SEQ ID NO:1) (zone A), probe A20 (SEQ ID NO:6) (zone B) or probe A21 (SEQ ID NO:7) (zone C).
Figure 6B:
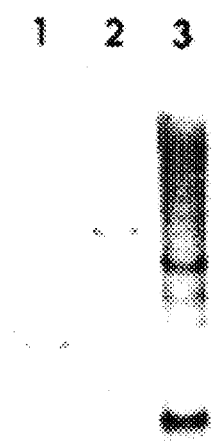
Figure 6C:
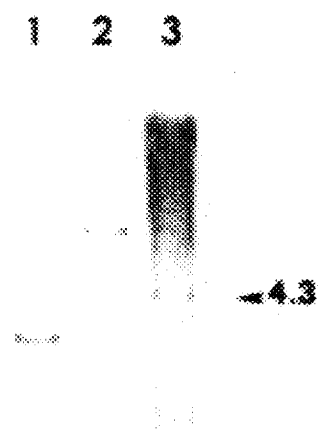

The three probes thus prepared were radio labelled and used in genomic DNA hybridization experiments (Southern blotting) in order to estimate their specificity towards the β3 gene. Genomic DNAs prepared from BALB/c mouse liver were digested with a restriction enzyme (BglII: lanes 1 of FIG. 6; BamHI: lanes 2 of FIG. 6); likewise, the genomic DNA isolated from A431 cells (human epidermoid line) was digested with BamHI (lanes 3 of FIG. 6); the fragments obtained were separated on agarose gel and transferred on to nylon membrane. The membrane was then hybridized with one of the radio labelled probes (A19: zone A, A20: zone B or A21: zone C of FIG. 6), washed under low stringency conditions and then autoradiographed. Each of these probes detects a single band on the BALB/c mouse genomic DNA (FIG. 6). In each of the cases, the size of the hybridization fragment (3.6 Kb with the enzyme BglII, 6.9 Kb with the enzyme BamHI, 13 Kb with the enzyme PstI and 4.1 Kb with SacI) corresponds to that of the murine β3-adrenergic gene which was cloned.

These results indicate that each of these three probes specifically detects the mouse β3-adrenergic gene. The presence of a single band in the mouse total DNA indicates that in the murine genome, there is no other sequence highly homologous to the β3-adrenergic gene. It can be concluded from this that only one copy of the RA-β3 gene exists in mice.

EXAMPLE 5

Construction of a Vector for Expressing the Murine RA-β3.

The study of the pharmacological properties of the product of the murine β3 gene requires that it is expressed at the surface of eukaryotic cells which possess all the elements necessary for translation of the signal. In order to be able to directly compare the properties of the murine and human β3-AR receptors, it was decided to express the mouse β3 gene in the CHO (Chinese Hamster Ovary) cell line which has already been used to analyse the human β3-AR receptor (see French Patent Application No. 89 00918).

In this system (FIG. 7), the coding region of the gene to be analysed is inserted between the SV40 viral promoter (this strong promoter makes it possible to obtain a high level of expression) and a polyadenylation site derived from the hepatitis B virus (HBsAg), into a plasmid also containing the gene encoding dihydrofolate reductase (DHFR, an enzyme which makes it possible for the cells to survive in a medium lacking glycine, hypoxanthine and thymidine).

Figure 7:
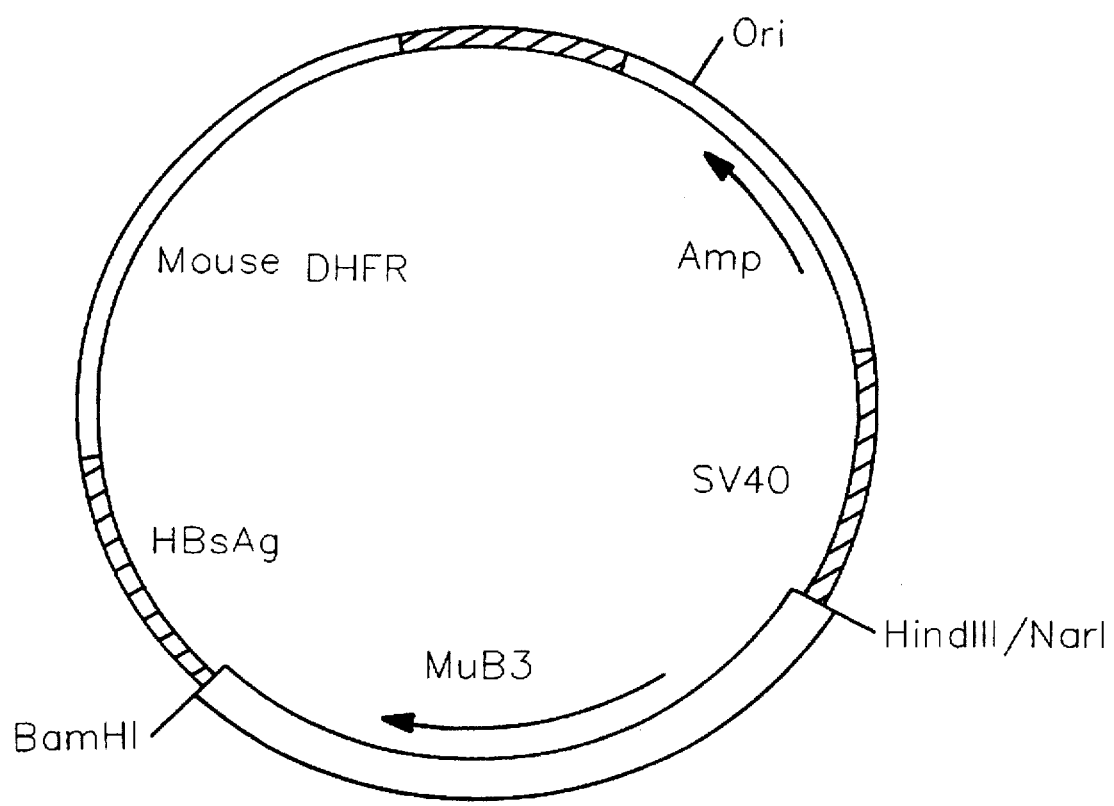
FIG. 7 is a schematic representation of plasmid pSTH-Muβ3.

The restriction map of the 2-Kb fragment which was sequenced (SEQ ID NO:1) (FIG. 2) indicates the presence of a NarI enzyme cleavage site at position 555, that is to say 15 nucleotides upstream of the coding region of the mouse β3 gene. The DNA of the clone MB1BB1 (2 Kb (SEQ ID NO:1) inserted into M13mp18) was digested with the enzymes NarI and BamHI in order to release the 1360-bp fragment (SEQ ID NO:4) containing the coding region of the β3 gene and a portion of the untranslated 3' region. This DNA fragment was purified and then inserted into the expression vector at the cleavage sites of the enzymes HindIII and BamHI (FIG. 7). As the ends generated by the enzymes NarI and HindIII are not compatible, care was taken, during the enzymatic digestion, to treat the NarI ends of the insert on the one hand, and the HindIII ends of the vector on the other hand, with polymerase I "Klenow" fragment so as to obtained blunt ends.

The recombinant plasmid pSTH-Muβ3 represented in FIG. 7 was thus obtained.

EXAMPLE 6

Chromosomal Location of the Murine RA-β3 Gene.

Procedure

For the chromosomal location of the murine RA-β3 gene, in situ hybridization is carried out on concanavalin A-stimulated lymphocytes in metaphase; these lymphocytes are derived from male WMP mice in which all the autosomes, with the exception of autosome 19, are in the form of Robertsonian translocations.

The lymphocytes are cultured at 37° C. for 72 h, with 5-bromodeoxyuridine (60 µg/ml) added at the 65th hour of culture.

The specific probe is the A21 probe as described in Example 4.

This probe is subcloned into the plasmid vector puC19, labelled with tritium by nick translation, so as to obtain a specific activity of $10^8$ d.p.m./µg and is used at a final concentration of 25 ng/ml of hybridization solution.

The hybridization of the metaphase cells, the washes and the staining are performed as described in MATTEI et al. (Human Genetics, 1985, 69, 268–271).

Location

The murine RA-β3 gene was located in the (8A2–8A4) region of chromosome 8 by in situ chromosomal hybridization, according to the procedure above.

In the 150 metaphase cells examined, there were 278 silver-stained spots associated with the chromosomes: 46 of these spots (16.5%) were located on chromosomes 8, and 32 of them (69.5%) in the (8A2–8A4) region (FIG. 8).

Figure 8A:
FIG. 8A shows partial mouse lymphocyte metaphase, and shows the specific site of hybridization of probe A21 (SEQ ID NO:7) to chromosome 8. In the left panel, the arrow indicates the silver-stained spots on the Giemsa-stained chromosomes after autoradiography.
Figure 8B:
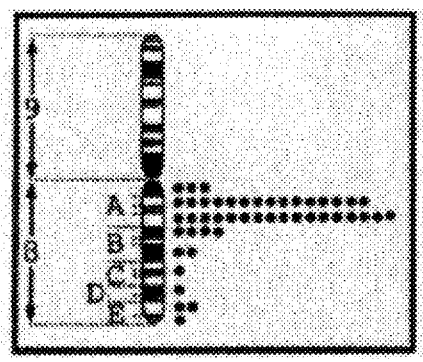
FIG. 8B identifies the stained chromosomes of FIG. 8A by R-banding.

FIG. 8 comprises in FIG. 8A, a partial mouse lymphocyte metaphase showing the specific site of hybridization to chromosome 8; on the left, the arrow indicates the silver-stained spots on the Giemsa-stained chromosomes, after autoradiography; on the right (FIG. 8B) the stained chromosomes are identified by "R-banding".

EXAMPLE 7

Pharmacology of the Murine RA-β3 Receptor

1. Tests Used a. Test for cAMP Accumulation preconfluent cells such as those described in Example 5 ($5\times10^5$) are incubated at 37° C. for 20 minutes in 0.5 ml of HANKS buffer containing 20 mM HEPES (pH 7.4), 1 mM ascorbic acid, 1 mM isobutylmethylxanthine and various concentrations of agonist.

After boiling for 5 min and centrifugation (4000 r.p.m., 10 min, 4° C.), the quantity of cAMP produced is determined using the Amersham cAMP kit.

For the study of the inhibition of cAMP accumulation, the cells are preincubated at 37° C. for 10 min with an antagonist, before the addition of 5 nM (−)-isoproterenol, followed by incubation for 20 min.

b. Test for the Binding of ICYP preconfluent cells such as those described in Example 5 ($10^5$) are incubated for 1 hour at 37° C. in a HANKS buffer containing 20 mM HEPES (pH 7.4), 1 mM ascorbic acid, 2 µM desipramine, 0.05% bovine serum albumin and 70–7000 pM (−)-[$^{125}$I]ICYP (2000 Ci/mmol, Amersham).

Non-specific binding is determined in the presence of 100 µM (−)-isoproterenol.

The incubations are stopped by dilution in cold PBS buffer and the bound ligand is separated from free [$^{125}$I] ICYP by filtration (Whatman GF/C filters impregnated with 0.3% polyethyleneimine).

The filters are washed 3 times with cold PBS buffer and the radioactivity is measured.

2. Pharmacological Profile

To determine the pharmacological profile of murine RA-β3, the coding region of its gene was inserted into an expression vector like that described in Example 5.

Figure 9:
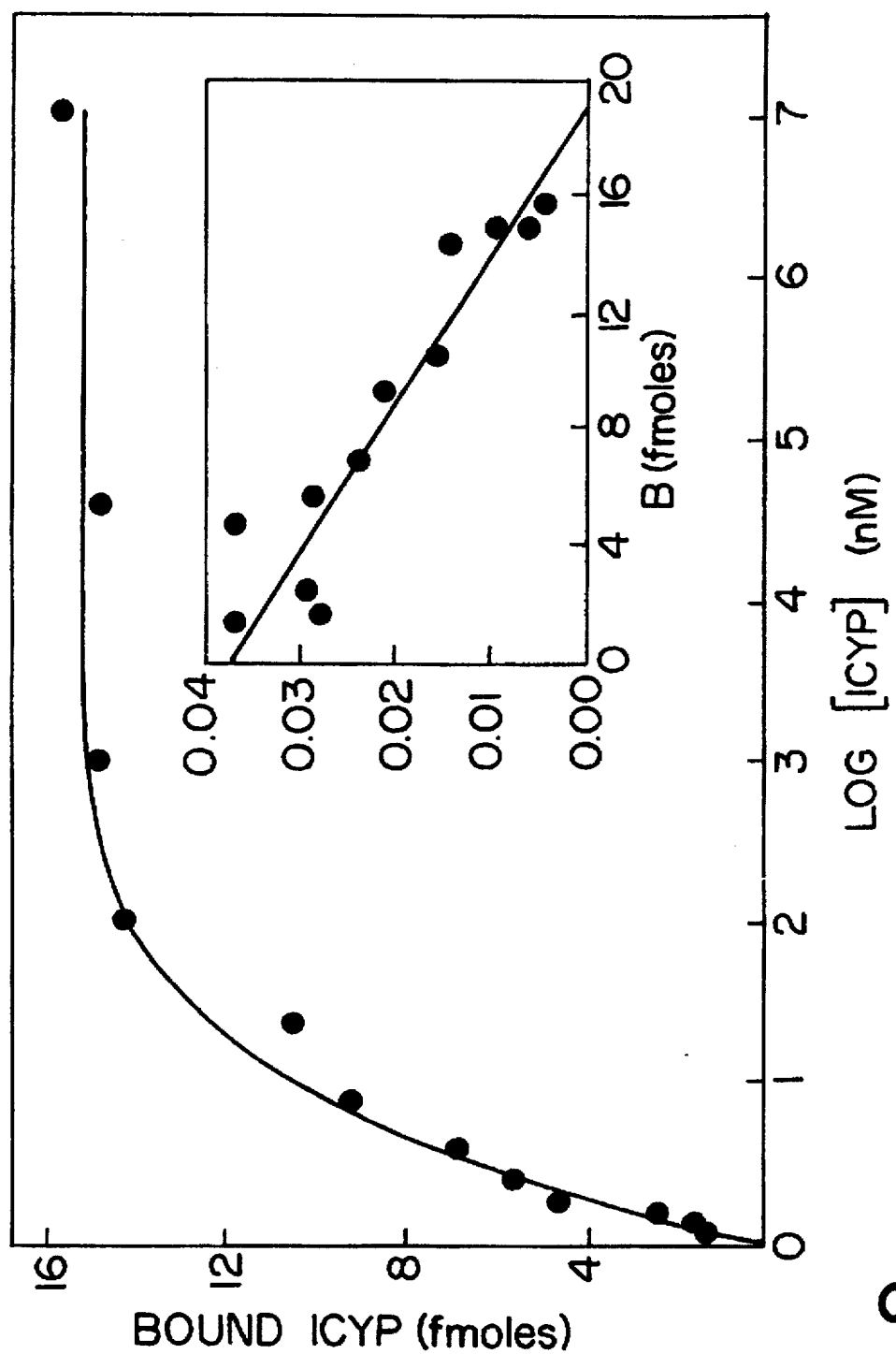
FIG. 9 graphs the binding to saturation of [$^{135}$I] ICYP to intact CHO-Muβ3 cells.

The binding to saturation of [$^{125}$I]iodocyanopindolol (ICYP) and the corresponding Scatchard analysis (FIG. 9, which comprises on the x-axis the log of ICYP concentration (nM) and on the y-axis the quantity of bound ICYP (fmol) (with Scatchard)) indicates that the CHO cells transfected in a stable manner (CHO-Muβ3) express 200,000±50,000 receptors/cell with a dissociation constant of 880±88 pM (mean±SEM, n=3).

Figure 10A:
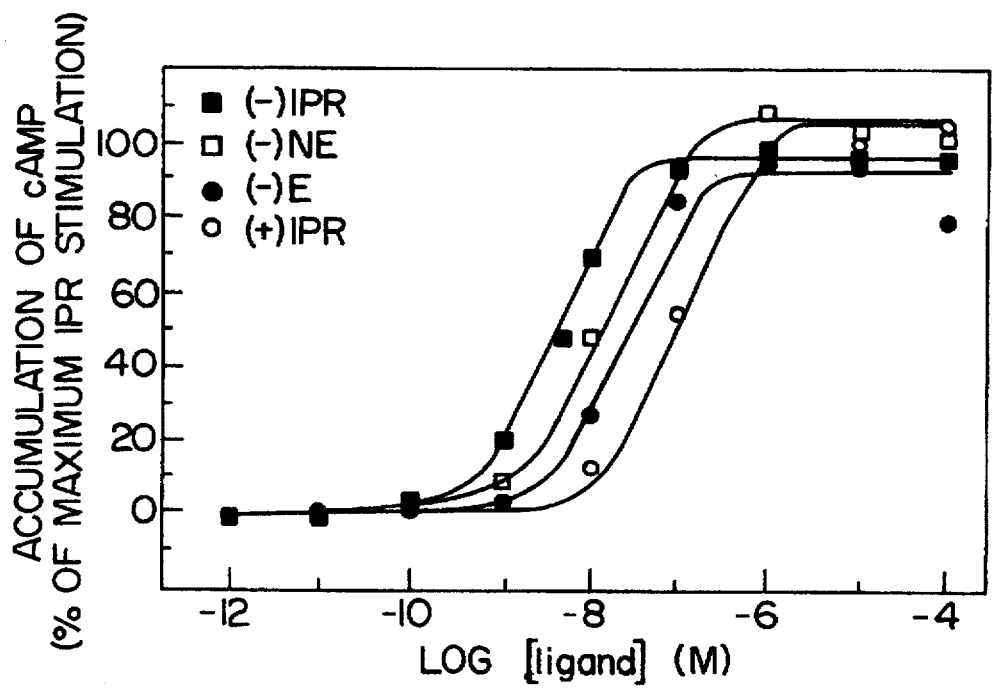
FIG. 10A graphs the accumulation of cAMP after exposure of CHO-Muβ3 cells to conventional β agonists in the presence of 5 nM (−)-isoproterenol, where solid boxes are (−)-isoproterenol, open boxes are (−)-noradrenalin, closed circles are (−)-adrenalin, and open circles are (+)-isoproterenol. The x-axis represents the log of the ligand concentration (M) and the y-axis represents the percentage cAMP accumulation.

The accumulation of cAMP is stimulated by incubation of the CHO-Muβ3 cells with isoproterenol, noradrenaline and adrenaline (FIG. 10A).

This stimulation is stereospecific since (−)-isoproterenol is 20 times more active than (+)-isoproterenol, as illustrated in Table II below:

TABLE II

| Ligands | CHO-Muβ3 | | CHO-Huβ3a | |
|---|---|---|---|---|
| | A.I. (% IPR) | $K_{act}$ or $K_i$ (nM) | A.I. (% NA) | $K_{act}$ or $K_i$ (nM) |
| Complete agonists: | | | | |
| BRL 37344 | 107.4 ± 8.1 | 0.4 ± 0.1 | 87.2 ± 15.4 | 5.9 ± 1.3 |

TABLE II-continued

|  | CHO-Muβ3 | | CHO-Huβ3a | |
| --- | --- | --- | --- | --- |
| Ligands | A.I. (% IPR) | $K_{act}$ or $K_i$ (nM) | A.I. (% NA) | $K_{act}$ or $K_i$ (nM) |
| (−)-isoproterenol | 100.0 ± 10.3 | 4.5 ± 1.9 | 90.2 ± 2.1 | 3.9 ± 0.4 |
| (−)-noradrenaline | 105.6 ± 5.6 | 12.9 ± 4.2 | 100 | 6.3 ± 0.7 |
| (−)-adrenalin | 90.6 ± 2.9 | 23.0 ± 0.3 | 100.4 ± 3.8 | 49.2 ± 5.3 |
| (+)-isoproterenol | 304.0 ± 10.2 | 99.0 ± 44.0 | 97.3 ± 10.9 | 111.0 ± 1.0 |
| Partial agonists |  |  |  |  |
| CGP 13177A | 74.9 ± 7.9 | 40.5 ± 8.7 | 67.6 ± 2.0 | 138.7 ± 44.3 |
| oxprenolol | 43.8 ± 6.1 | 535.3 ± 79.3 | 53.3 ± 6.8 | 76.6 ± 12.6 |
| pindolol | 35.1 ± 3.1 | 998.7 ± 197.0 | 55.0 ± 5.3 | 153.0 ± 12.0 |
| Antagonists: |  |  |  |  |
| Propranolol |  | 450.0 ± 221.2 | ND |  |
| ICI 116551 |  | 4968.9 ± 137.4 |  | 770.0 ± 80.0 |
| CGP 00712A |  | 6424.6 ± 583.6 |  | 6700.0 ± 870.0 |

In this Table II, A.I. represents the intrinsic activity and corresponds to the percentage of maximum stimulation obtained for each agonist as a function of the maximum effect of (−)-isoproterenol, the basal and maximum concentrations of cAMP, which is induced by isoproterenol, being 25 and 500 pmol per million cells, respectively.

The $K_{act}$ values correspond to the agonist concentration giving 50% of the maximum stimulation.

The $K_i$ values are calculated according to CHENG and PRUSOFF (Biochem. Pharmacol., 1973, 32, 3099–3108), with $IC_{50}$ values defined as the antagonist concentration required to induce a 50% inhibition of the maximum activity obtained with (−)-isoproterenol (5 nM).

Figure 10B:
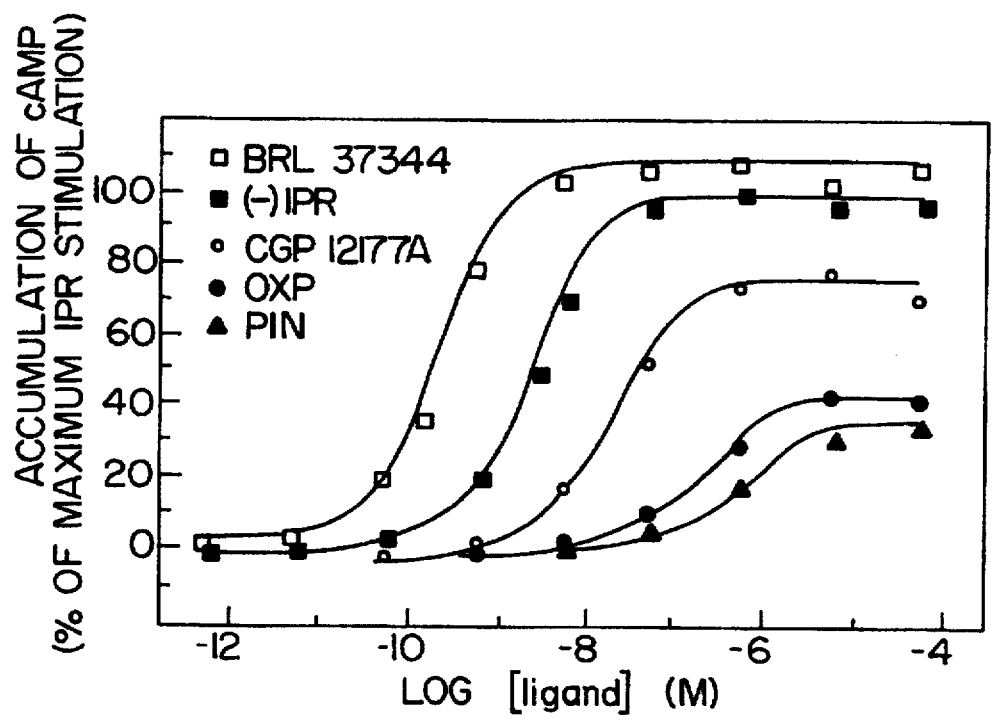
FIG. 10B graphs the accumulation of cAMP after exposure of CHO-Muβ3 cells to atypical β agonists in the presence of 5 nM (−)-isoproterenol, where solid boxes are (−)-isoproterenol, open boxes are BRL 3733, closed circles are oxyprenolol, open circles are CGP 12177A, and closed triangles are pindolol. The x-axis represents the log of the ligand concentration (M) and the y-axis represents the percentage cAMP accumulation.

The agonist BRL 37344 is 10 times more active than (−)-isoproterenol (IPR) for inducing cAMP accumulation (FIG. 10B, Table II).

The β1 and β2 antagonists CGP 12177A, oxprenolol and pindolol behave like partial agonists of the murine RA-β3, with a maximum stimulation of cAMP accumulation of 77%, 45% and 36%, respectively, of that for (−)-isoproterenol.

For other β antagonists such as propranolol (nonselective), ICI 118551 (β2-selective) and CGP 20712A (β1-selective) (FIG. 10C), micromolar concentrations are required to inhibit the cAMP accumulation induced by (−)-isoproterenol.

FIGS. 10A and 10B comprise, on the x-axis, the log of the ligand concentration (M) and on the y-axis, the percentage cAMP accumulation (percentage of the maximum response induced by isoproterenol).

FIG. 10A corresponds to conventional β-agonists (■: (−)-isoproterenol; □: (−)-noradrenalin; ●: (−)-adrenalin; ○: (+)-isoproterenol); FIG. 10B corresponds to atypical β-agonists (□: BRL 37344; ■: (−)-isoproterenol; ○: CGP 12177A; ●: oxprenolol; ▲: pindolol).

Figure 10C:
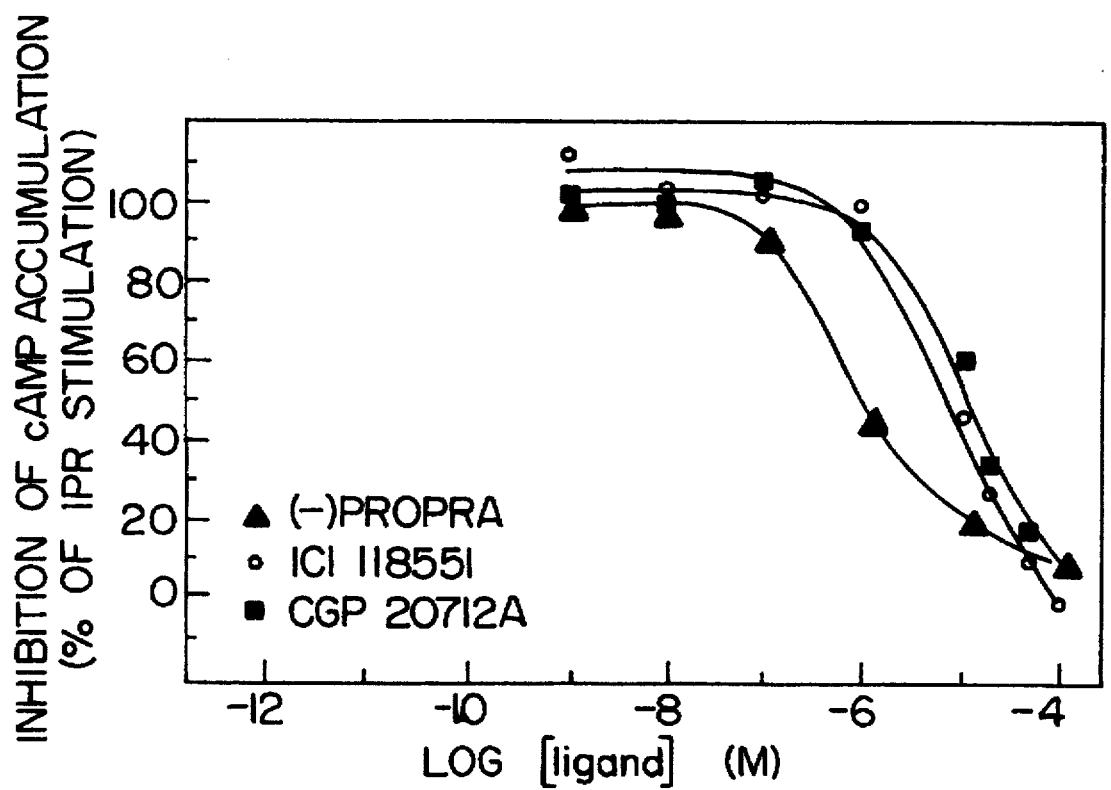
FIG. 10C demonstrates that micromolar amounts of some β antagonists inhibit the cAMP accumulation seen after exposure of CHO-Muβ3 cells to 5 nM (−)-isoproterenol. The x-axis represents the log of the ligand concentration (M) and the y-axis represents the percentage inhibition of cAMP; closed triangles are (−)-isopropranolol, open circles are ICI 118551, and closed squares are CGP 20712A.

FIG. 10C comprises, on the x-axis, the log of the ligand concentration (M) and on the y-axis, the percentage inhibition of cAMP accumulation (percentage of the response induced by 5 nM isoproterenol) and corresponds to the action of β antagonists in the presence of 5 nM (−)-isoproterenol (▲: (−)-propranolol; ○: ICI 118551; ■: CGP 20712A).

3. Tissue Distribution

Hybridization analysis, with the A21 probe (SEQ ID NO:7), of the total RNA (Northern technique) extracted from various mouse tissues reveals a major 2.2 Kb band both in the white adipose tissue and in the brown adipose tissue.

Figure 11:
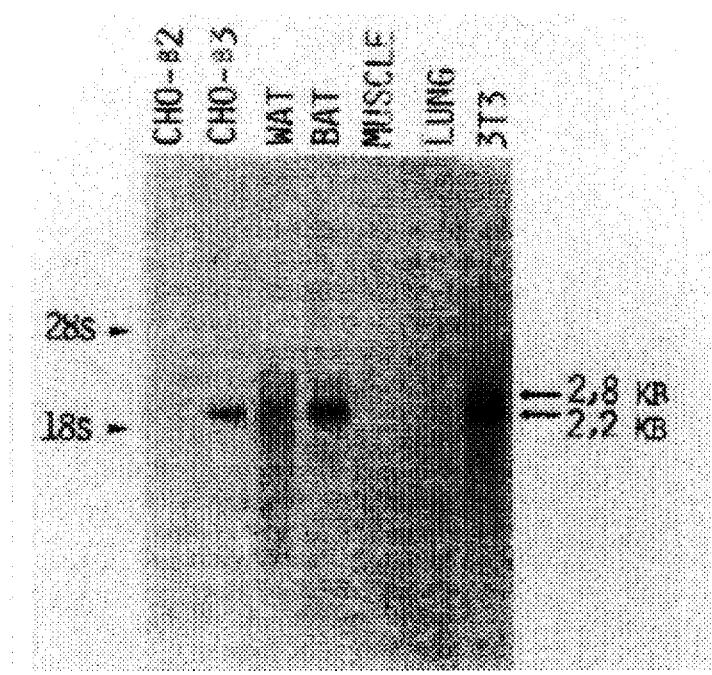
FIG. 11 shows a Norther blot hybridization of the probe A21 (SEQ ID NO:7) with the total RNA of various mouse tissues (white adipose tissue(WAT); brown adipose tissue (BAT); muscle; and lung), and of the adipose cell lines 3T3-F442A (3T3).

In the differentiated adipocytes 3T3-F442A, a major transcript of similar size (2.2 kb) as well as a minor 2.8-kb transcript are detected (FIG. 11).

No hybridization signal is detected in the total RNA prepared from other tissues (femoral muscle, lungs, liver, ileum, colon, brain, stomach, heart and kidneys).

The above pharmacological profile of the murine RA-β3 suggests a receptor which acts on lipolysis (receptor of the atypical RA-β type involved in the regulation of the energy consumption of rodent adipose cells).

For example, the potent agonist effect of BRL 37344 on RA-β3 is reminiscent of its effectiveness in the stimulation of cAMP accumulation, of lipolysis and of thermogenesis in obese rat cells.

The RA-β3-specific agonist CGP 12177A stimulates lipolysis and adenylate cyclase activity.

FIG. 11 represents a hybridization between the A21 probe (SEQ ID NO:7) and the total RNA (30 μg) of mouse tissues or of the adipose cell lines 3T3-F442A (on day 7 of the differentiation), after RNA transfer (Northern technique).

In this FIG. 11, WAT means white adipose tissue; BAT means brown adipose tissue.

The sizes of the transcripts which hybridize are indicated in kb on the right, and the position of the 28S and 18S rRNA bands is represented on the left hand side of the figure.

4. Comparison with Human RA-β3 a. Points in Common

Comparison of the pharmacological properties is illustrated in Table II above.

The labelled β-adrenergic antagonist [$^{125}$I]ICYP binds to murine RA-β3 and to human RA-β3 with a similar affinity, which is of the order of 10 to 20 times less than that obtained with RA-β1 and RA-β2.

Likewise, antagonists such as propranolol, ICI 118551 and CGP 20712A are weak inhibitors of the isoproterenol-induced accumulation of cAMP.

Like the human receptor, murine RA-β3 can be activated by the β1 and β2 antagonists: CGP 12177A, oxprenolol and pindolol.

These two types of receptors (murine and human) have a low stereoselectivity.

b. Differences

In the transmembrane domains, which are involved in the binding of the ligand, the presence of 12 substitutions can be noted between the two receptors.

Figure 5:
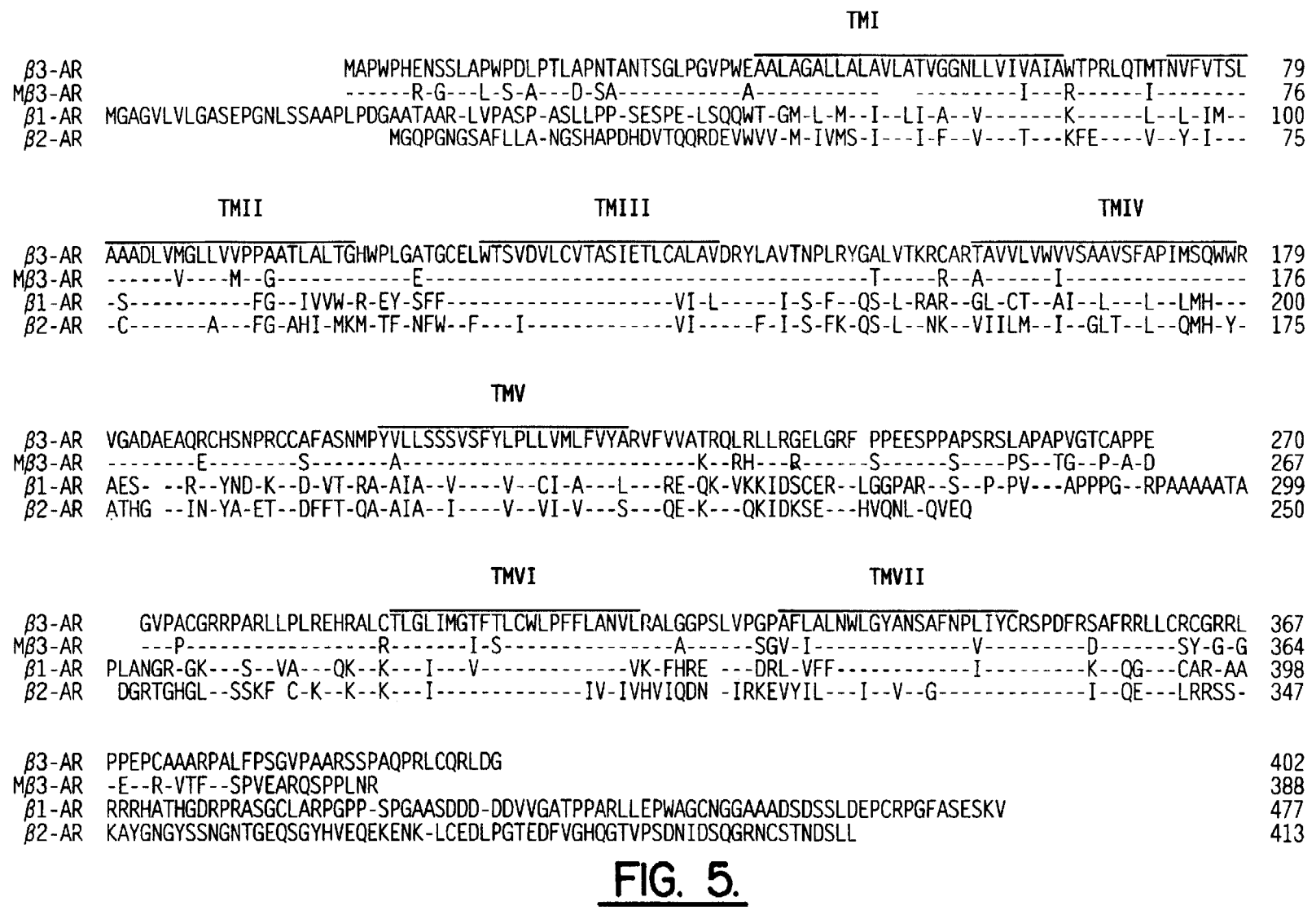

Furthermore, the 30 C-terminal residues of the mouse β3 do not exhibit any homology with the C-terminal tail of the human β3 receptor (FIG. 5). The murine RA-β3 comprises a tyrosine residue in position 360 of the amino acid sequence, which does not exist in the human RA-β3 sequence (FIG. 5).

The most striking differences appear in the intracytoplasmic loops near the transmembrane regions where 3 arginine residues (positions 61, 150 and 289 of the murine RA-β3) are replaced by a tryptophan, a cysteine and another cysteine, respectively, in the human RA-β3.

Such differences could be responsible for pharmacological modifications such as that of the increased potency of the agonist BRL 37344 in mice, which makes it possible in particular to study the metabolism of adipose tissue; indeed, murine RA-β3 is, surprisingly, sufficiently related to human RA-β3 for such a study.

As evident from the above, the invention is not in the least limited to the implementations, embodiments and applications which have just been described more explicitly; on the contrary, it embraces all the variants which may occur to a specialist in this field without departing from the framework or the scope of the present invention.

28

International Application No: PCT

MICROORGANISMS

Optional Sheet in connection with the microorganism referred to on page 11, line 24 of the description

A. IDENTIFICATION OF DEPOSIT

Further deposits are identified on an additional sheet ☐

Name of depositary institution

Collection Nationale de Cultures de Micro-organismes

Address of depositary institution (including postal code and country)

28 rue du Docteur Roux, 75724 PARIS Cédex 15 (FRANCE)

Date of deposit
14 January 1991

Accession Number
I-1026

B. ADDITIONAL INDICATIONS (leave blank if not applicable). This information is continued on a separate attached sheet ☐

"With regard to the nominations in which a European patent is applied for, until the publication of the mention of the grant of the European patent or until the date on which the application shall be refused or withdrawn or shall be deemed to be withdrawn, a sample of the deposited microorganism shall be available only by the issue of a sample to an expert nominated by the requester. (Rule 28.4) of the EPC)".

C. DESIGNATED STATES FOR WHICH INDICATIONS ARE MADE (If the indications are not for all designated States)

EUROPE
JAPAN
UNITED STATES OF AMERICA

D. SEPARATE FURNISHING OF INDICATIONS (leave blank if not applicable)

The indications listed below will be submitted to the International Bureau later (Specify the general nature of the indications e.g. "Accession Number of Deposit")

E. ☐ This sheet was received with the international application when filed (to be checked by the receiving Office)

(illegible signature)
(Authorized Officer)

☐ The date of receipt (from the applicant) by the International Bureau is was (Authorized Officer)

Form PCT/RO/134 (January 1981)

We claim:

1. An isolated DNA molecule consisting of the nucleotide sequence of SEQ ID NO:1 and encoding the murine β3-adrenergic receptor protein.

2. An isolated DNA molecule consisting of SEQ ID NO:1 and comprising the following unique restriction sites: AlwN I, Sac I, Stu I, Dra I, Mse I, Bbe I, Nar I, Xcm I, NCo I, BspM I, Afl III, Pvu I, Nhe I, BstE II, BspH I, Bsm I, NSp7524 I, NSpH I, Xho I, Sac II, Eag I, Nae I, PaeR7 I, EcoN I, Fsp I, Bbv II, Nru I, Drd I, BamH I.

3. An isolated DNA molecule consisting of the nucleotide sequence of SEQ ID NO:3.

4. An isolated DNA molecule consisting of the sequence of SEQ ID NO:4.

5. An isolated DNA molecule consisting of the sequence of SEQ ID NO:6.

6. An isolated DNA molecule consisting of the sequence of SEQ ID NO:7.

7. An isolated nucleotide probe selected from the group of nucleotide probes consisting of SEQ ID NO:1, SEQ ID NO:3, SEQ ID NO:4, SEQ ID NO:6 and SEQ ID NO:7.

8. An isolated and purified polypeptide having a β3-adrenergic receptor activity and having the amino acid sequence of SEQ ID NO:2.

9. A fragment of a polypeptide having SEQ ID NO:2, said fragment comprising at least 99 contiguous amino acids of SEQ ID NO:2.

10. An isolated and purified polypeptide having the amino acid sequence of SEQ ID NO:9.

11. An expression vector comprising a nucleotide sequence of SEQ ID NO:1.

12. A host cell transformed by an expression vector according to claim 11.

13. A transformed host cell according to claim 12, wherein said host cell is a CHO (Chinese hamster ovary) cell.

14. A recombinant vector comprising a replication origin selected from the group consisting of bacterial and eukaryotic replication origins; a nucleic acid encoding a selectable marker; a promoter selected from the group consisting of bacterial and eukaryotic promoters; and a nucleotide sequence of SEQ ID NO:1.

15. A recombinant vector comprising, in the 5' to 3' direction, an appropriate replication origin, a gene for resistance to ampicillin, the viral promoter SV40, a nucleotide sequence having the sequence of SEQ ID NO:1, a polyadenylation site derived from the hepatitis B virus (HBSAG) and the gene which encodes dihydrofolate reductase (DHFR), wherein expression of dihydrofolate reductase permits survival of cells in a medium lacking glycine, hypoxanthine and thymidine.

16. The vector deposited as I-1026 with the Collection Nationale de Cultures de Microorganisms, Institut Pasteur.

17. A method of assaying a substance for agonist activity towards a polypeptide having a β3-adrenergic receptor activity, which method comprises:

placing the substance in contact with a transformed host cell expressing murine β3 adrenergic receptor polypeptide encoded by SEQ ID NO:1, SEQ ID NO:3 or SEQ ID NO:4, under conditions which permit binding between β3 adrenergic receptor protein binding sites and an agonist thereto; and measuring the quantity of cAMP produced, wherein accumulation of cAMP indicates formation of agonist-polypeptide complexes and indicates said substance is an agonist for murine β3 adrenergic receptor polypeptide.

18. A process for studying the binding affinity of a compound for a polypeptide having a β3-adrenergic receptor activity, which process comprises:

transforming a host cell by an expression vector comprising a nucleotide sequence of SEQ ID NO:1;

culturing said transformed host cell under conditions which permit the expression of the β3-adrenergic receptor protein encoded by said nucleotide sequence, and the transfer of the expressed β3-adrenergic receptor protein to the membrane of the said transformed host cell so that transmembrane sequences of the β3 receptor-adrenergic protein are embedded in the cell membranes of the transformed host cell;

placing said transformed host cell in contact with said compound; and measuring the quantity of said compound bound to said β3-adrenergic receptor protein.

19. A kit for assaying the binding affinity of a compound for a polypeptide having murine β3-adrenergic receptor activity and encoded by SEQ ID NO:1, SEQ ID NO:3 or SEQ ID NO:4, which kit comprises:

a culture of host cells transformed by an expression vector according to claim 16; and a control ligand having a determined binding affinity for said peptide.

20. An isolated nucleotide probe consisting of a sequence selected from the group consisting of SEQ ID NO:1, SEQ ID NO:3, SEQ ID NO:4, SEQ ID NO:6 and SEQ ID NO:7 said probe hybridizing to DNA of SEQ ID NO:1 but not to genes encoding β1- and β2-adrenergic receptor proteins or to messenger RNA encoding said β1- and β2-adrenergic receptor proteins, under hybridization conditions of 750 mM of NaCL, 75 mM of trisodium citrate, 50 µg/ml of salmon sperm DNA, 50 mM of sodium phosphate, 1 mM of sodium pyrophosphate, 100 µM of ATP, 10% to 25% formamide, 1% Ficoll, 1% polyvinylpyrrolidione, 1% bovine serum albumin, for 14 to 16 hours at 42° C.

21. An isolated nucleotide probe consisting of more than 100 contiguous nucleotides of SEQ ID NO:1.

22. A polypeptide having SEQ ID NO:2, wherein BRL 37344 stimulates adenylate cyclase and cAMP accumulation at least 10 times more than that stimulated by (1)-isoproterenol in Chinese Hamster Ovary (CHO) cells transfected with said polypeptide under conditions wherein said cells are incubated for 20 minutes in a Hank's medium containing 20 mM HEPES buffered at pH 7.4, 1 mM of ascorbic acid, 1 mM isobutylmethylxanthine, and with concentrations of BRL 37344 higher than $10^{-12}$M.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1920 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 568..1731

( x i ) SEQUENCE DESCRIPTION: SEQ ID NO:1:

```
GATCTGTAAT  CCCAGCACTG  GGGAGGTTGA  GGCAGAAGGA  TCTGGAGGTC  CAGACCAATC      60

TGGGCAACAT  ATAGAAAGAC  TATCTCAAAC  AATAAGATAC  CTTAGGGAGA  GCATCCAAGC     120

AGAAGAGGGG  CTATCTTGGA  TGGTTTGGGT  TGTTCGGTTT  TGTTTTGGTT  TGTTTCTGGA     180

TGGTTGCCTT  CCTTGTTGGG  TAAAGGATAG  GGTGCGGGGG  TTTCTCTTCT  TTGCAGGGTT     240

GCCTCAGGTT  CTGCCAGGAA  GGAGCTGCTG  AGCTCCAGGA  AACCGGTGCT  GAGGGAGTGT     300

CAAGACAGGA  CGCCCCTCTC  CACCCTCCAA  TTCCCACCAG  AGGCCTCTCT  TGTGACTATT     360

GGACGCTGTT  CCTTTAAAAG  CAGCCACTCC  TCCCGGCAAC  TAGGGTGTAC  ATGGGGGGTG     420

AGATGGAGGG  AAGCTGACAG  ACTTACCCCA  GCAATTAGGG  AAGATGGCCC  AGGCTGGAAG     480

AGTCGCTCCC  AAGCCCTACT  GTCCCCTTCC  CTAAGCCAGC  GGGTCTGGGG  AGGAGGGGGA     540

ACCTTCCCAC  CCCAGGCGCC  ACACGAG ATG GCT CCG TGG CCT CAC AGA AAC            591
                               Met Ala Pro Trp Pro His Arg Asn
                                1               5
```

| | | | | | | | | | | | | | | | | |
|---|---|---|---|---|---|---|---|---|---|---|---|---|---|---|---|---|
| GGC | TCT | CTG | GCT | TTG | TGG | TCG | GAC | GCC | CCT | ACC | CTG | GAC | CCC | AGT | GCA | 639 |
| Gly | Ser | Leu | Ala | Leu | Trp | Ser | Asp | Ala | Pro | Thr | Leu | Asp | Pro | Ser | Ala | |
| | 10 | | | | 15 | | | | | 20 | | | | | | |
| GCC | AAC | ACC | AGT | GGG | TTG | CCA | GGA | GTA | CCA | TGG | GCA | GCG | GCA | TTG | GCT | 687 |
| Ala | Asn | Thr | Ser | Gly | Leu | Pro | Gly | Val | Pro | Trp | Ala | Ala | Ala | Leu | Ala | |
| 25 | | | | | 30 | | | | | 35 | | | | | 40 | |
| GGG | GCA | TTG | CTG | GCG | CTG | GCC | ACG | GTG | GGA | GGC | AAC | CTG | CTG | GTA | ATC | 735 |
| Gly | Ala | Leu | Leu | Ala | Leu | Ala | Thr | Val | Gly | Gly | Asn | Leu | Leu | Val | Ile | |
| | | | | 45 | | | | | 50 | | | | | 55 | | |
| ATA | GCC | ATC | GCC | CGC | ACG | CCG | AGA | CTA | CAG | ACC | ATA | ACC | AAC | GTG | TTC | 783 |
| Ile | Ala | Ile | Ala | Arg | Thr | Pro | Arg | Leu | Gln | Thr | Ile | Thr | Asn | Val | Phe | |
| | | | | 60 | | | | 65 | | | | | 70 | | | |
| GTG | ACT | TCA | CTG | GCC | GCA | GCT | GAC | TTG | GTA | GTG | GGA | CTC | CTC | GTA | ATG | 831 |
| Val | Thr | Ser | Leu | Ala | Ala | Ala | Asp | Leu | Val | Val | Gly | Leu | Leu | Val | Met | |
| | | 75 | | | | | 80 | | | | | 85 | | | | |
| CCA | CCA | GGG | GCC | ACA | TTG | GCG | CTG | ACT | GGC | CAT | TGG | CCC | TTG | GGC | GAA | 879 |
| Pro | Pro | Gly | Ala | Thr | Leu | Ala | Leu | Thr | Gly | His | Trp | Pro | Leu | Gly | Glu | |
| | | 90 | | | | 95 | | | | | 100 | | | | | |
| ACT | GGT | TGC | GAA | CTG | TGG | ACG | TCA | GTG | GAC | GTG | CTC | TGT | GTA | ACT | GCT | 927 |
| Thr | Gly | Cys | Glu | Leu | Trp | Thr | Ser | Val | Asp | Val | Leu | Cys | Val | Thr | Ala | |
| 105 | | | | 110 | | | | | 115 | | | | | 120 | | |
| AGC | ATC | GAG | ACC | TTG | TGC | GCC | CTG | GCT | GTG | GAC | CGC | TAC | CTA | GCT | GTC | 975 |
| Ser | Ile | Glu | Thr | Leu | Cys | Ala | Leu | Ala | Val | Asp | Arg | Tyr | Leu | Ala | Val | |
| | | | | 125 | | | | | 130 | | | | | 135 | | |
| ACC | AAC | CCT | TTG | CGT | TAC | GGC | ACG | CTG | GTT | ACC | AAG | CGC | CGC | GCC | CGC | 1023 |
| Thr | Asn | Pro | Leu | Arg | Tyr | Gly | Thr | Leu | Val | Thr | Lys | Arg | Arg | Ala | Arg | |

|     |     |     |     |     |     | 140 |     |     |     |     |     | 145 |     |     |     |     |     | 150 |     |     |     |      |
| --- | --- | --- | --- | --- | --- | --- | --- | --- | --- | --- | --- | --- | --- | --- | --- | --- | --- | --- | --- | --- | --- | ---- |
| GCG | GCA | GTT | GTC | CTG | GTG | TGG | ATC | GTG | TCC | GCT | GCC | GTG | TCC | TTT | GCG |     |     |     |     |     |     | 1071 |
| Ala | Ala | Val | Val | Leu | Val | Trp | Ile | Val | Ser | Ala | Ala | Val | Ser | Phe | Ala |     |     |     |     |     |     |      |
|     |     | 155 |     |     |     |     | 160 |     |     |     |     | 165 |     |     |     |     |     |     |     |     |     |      |

```
GCG GCA GTT GTC CTG GTG TGG ATC GTG TCC GCT GCC GTG TCC TTT GCG                    1071
Ala Ala Val Val Leu Val Trp Ile Val Ser Ala Ala Val Ser Phe Ala
        155             160             165

CCC ATC ATG AGC CAG TGG TGG CGT GTA GGG GCA GAT GCC GAG GCA CAG                    1119
Pro Ile Met Ser Gln Trp Trp Arg Val Gly Ala Asp Ala Glu Ala Gln
    170             175             180

GAA TGC CAC TCC AAT CCG CGC TGC TGT TCC TTT GCC TCC AAC ATG CCC                    1167
Glu Cys His Ser Asn Pro Arg Cys Cys Ser Phe Ala Ser Asn Met Pro
185             190             195             200

TAT GCG CTG CTC TCC TCC TCC GTC TCC TTC TAC CTT CCC CTC CTT GTG                    1215
Tyr Ala Leu Leu Ser Ser Ser Val Ser Phe Tyr Leu Pro Leu Leu Val
            205             210             215

ATG CTC TTC GTC TAT GCT CGA GTG TTC GTT GTG GCT AAG CGC CAA CGG                    1263
Met Leu Phe Val Tyr Ala Arg Val Phe Val Val Ala Lys Arg Gln Arg
        220             225             230

CAT TTG CTG CGC CGG GAA CTG GGC CGC TTC TCG CCC GAG GAG TCT CCG                    1311
His Leu Leu Arg Arg Glu Leu Gly Arg Phe Ser Pro Glu Glu Ser Pro
            235             240             245

CCG TCT CCG TCG CGC TCT CCG TCC CCT GCC ACA GGC GGG ACA CCC GCG                    1359
Pro Ser Pro Ser Arg Ser Pro Ser Pro Ala Thr Gly Gly Thr Pro Ala
250             255             260

GCA CCG GAT GGA GTG CCC CCC TGC GGC CGG CGG CCT GCG CGC CTC CTG                    1407
Ala Pro Asp Gly Val Pro Pro Cys Gly Arg Arg Pro Ala Arg Leu Leu
265             270             275             280

CCA CTC CGG GAA CAC CGC GCC CTG CGC ACC TTA GGT CTC ATT ATG GGC                    1455
Pro Leu Arg Glu His Arg Ala Leu Arg Thr Leu Gly Leu Ile Met Gly
            285             290             295

ATC TTC TCT CTG TGC TGG CTG CCC TTC TTC CTG GCC AAC GTG CTG CGC                    1503
Ile Phe Ser Leu Cys Trp Leu Pro Phe Phe Leu Ala Asn Val Leu Arg
            300             305             310

GCA CTC GCG GGG CCC TCT CTA GTT CCC AGC GGA GTT TTC ATC GCC CTG                    1551
Ala Leu Ala Gly Pro Ser Leu Val Pro Ser Gly Val Phe Ile Ala Leu
        315             320             325

AAC TGG CTG GGC TAT GCC AAC TCC GCC TTC AAC CCG GTC ATC TAC TGC                    1599
Asn Trp Leu Gly Tyr Ala Asn Ser Ala Phe Asn Pro Val Ile Tyr Cys
    330             335             340

CGC AGC CCG GAC TTT CGC GAC GCC TTC CGT CGT CTT CTG TGT AGC TAC                    1647
Arg Ser Pro Asp Phe Arg Asp Ala Phe Arg Arg Leu Leu Cys Ser Tyr
345             350             355             360

GGT GGC CGT GGA CCG GAG GAG CCA CGC GCA GTC ACC TTC CCA GCC AGC                    1695
Gly Gly Arg Gly Pro Glu Glu Pro Arg Ala Val Thr Phe Pro Ala Ser
            365             370             375

CCT GTT GAA GCC AGG CAG AGT CCA CCG CTC AAC AGG TAGGGACAC                          1741
Pro Val Glu Ala Arg Gln Ser Pro Pro Leu Asn Arg
        380             385

GAGCGGGGA  CCGGAGTCTC  TGGGTGGGGA  CGTCTCTGTC  TCTATTTTTG  AGTTTGGAGA              1801

TTGGGGGAGG  GGAAGATGTA  GATGGGGGTG  CGGTGTGTGT  GTGGGTGGGG  GGTGGCCTTT             1861

GTCTTGAGAG  GACAGAAAAG  AGGTAGGAAC  TAAAACGGGC  CCTTTCTCTT  CTTGGATCC              1920
```

( 2 ) INFORMATION FOR SEQ ID NO:2:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ala | Pro | Trp | Pro 5 | His | Arg | Asn | Gly | Ser 10 | Leu | Ala | Leu | Trp | Ser 15 | Asp |
| Ala | Pro | Thr | Leu 20 | Asp | Pro | Ser | Ala | Asn 25 | Thr | Ser | Gly | Leu 30 | Pro | Gly |
| Val | Pro | Trp 35 | Ala | Ala | Ala | Leu 40 | Gly | Ala | Leu | Leu 45 | Ala | Leu | Ala | Thr |
| Val | Gly 50 | Gly | Asn | Leu | Leu | Val 55 | Ile | Ile | Ala | Ile | Ala 60 | Arg | Thr | Pro | Arg |
| Leu 65 | Gln | Thr | Ile | Thr | Asn 70 | Val | Phe | Val | Thr | Ser 75 | Leu | Ala | Ala | Ala | Asp 80 |
| Leu | Val | Val | Gly | Leu 85 | Leu | Val | Met | Pro | Pro 90 | Gly | Ala | Thr | Leu | Ala 95 | Leu |
| Thr | Gly | His | Trp 100 | Pro | Leu | Gly | Glu | Thr 105 | Gly | Cys | Glu | Leu | Trp 110 | Thr | Ser |
| Val | Asp | Val 115 | Leu | Cys | Val | Thr | Ala 120 | Ser | Ile | Glu | Thr | Leu 125 | Cys | Ala | Leu |
| Ala | Val 130 | Asp | Arg | Tyr | Leu | Ala 135 | Val | Thr | Asn | Pro | Leu 140 | Arg | Tyr | Gly | Thr |
| Leu 145 | Val | Thr | Lys | Arg | Arg 150 | Ala | Arg | Ala | Ala | Val 155 | Val | Leu | Val | Trp | Ile 160 |
| Val | Ser | Ala | Ala | Val 165 | Ser | Phe | Ala | Pro | Ile 170 | Met | Ser | Gln | Trp | Trp 175 | Arg |
| Val | Gly | Ala | Asp 180 | Ala | Glu | Ala | Gln | Glu 185 | Cys | His | Ser | Asn | Pro 190 | Arg | Cys |
| Cys | Ser | Phe 195 | Ala | Ser | Asn | Met | Pro 200 | Tyr | Ala | Leu | Leu | Ser 205 | Ser | Ser | Val |
| Ser | Phe 210 | Tyr | Leu | Pro | Leu | Leu 215 | Val | Met | Leu | Phe | Val 220 | Tyr | Ala | Arg | Val |
| Phe 225 | Val | Val | Ala | Lys | Arg 230 | Gln | Arg | His | Leu | Leu 235 | Arg | Arg | Glu | Leu | Gly 240 |
| Arg | Phe | Ser | Pro | Glu 245 | Glu | Ser | Pro | Pro | Ser 250 | Pro | Ser | Arg | Ser | Pro 255 | Ser |
| Pro | Ala | Thr | Gly 260 | Gly | Thr | Pro | Ala | Ala 265 | Pro | Asp | Gly | Val | Pro 270 | Pro | Cys |
| Gly | Arg | Arg 275 | Pro | Ala | Arg | Leu | Leu 280 | Pro | Leu | Arg | Glu | His 285 | Arg | Ala | Leu |
| Arg | Thr 290 | Leu | Gly | Leu | Ile | Met 295 | Gly | Ile | Phe | Ser | Leu 300 | Cys | Trp | Leu | Pro |
| Phe 305 | Phe | Leu | Ala | Asn | Val 310 | Leu | Arg | Ala | Leu | Ala 315 | Gly | Pro | Ser | Leu | Val 320 |
| Pro | Ser | Gly | Val | Phe 325 | Ile | Ala | Leu | Asn | Trp 330 | Leu | Gly | Tyr | Ala | Asn 335 | Ser |
| Ala | Phe | Asn | Pro 340 | Val | Ile | Tyr | Cys | Arg 345 | Ser | Pro | Asp | Phe | Arg 350 | Asp | Ala |
| Phe | Arg | Arg 355 | Leu | Leu | Cys | Ser | Tyr 360 | Gly | Gly | Arg | Gly | Pro 365 | Glu | Glu | Pro |
| Arg | Ala 370 | Val | Thr | Phe | Pro | Ala 375 | Ser | Pro | Val | Glu | Ala 380 | Arg | Gln | Ser | Pro |
| Pro | Leu | Asn | Arg 385 | | | | | | | | | | | |

( 2 ) INFORMATION FOR SEQ ID NO:3:

( i ) SEQUENCE CHARACTERISTICS:
( A ) LENGTH: 1164 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| ATGGCTCCGT | GGCCTCACAG | AAACGGCTCT | CTGGCTTTGT | GGTCGGACGC | CCCTACCCTG | 60 |
| GACCCCAGTG | CAGCCAACAC | CAGTGGGTTG | CCAGGAGTAC | CATGGGCAGC | GGCATTGGCT | 120 |
| GGGGCATTGC | TGGCGCTGGC | CACGGTGGGA | GGCAACCTGC | TGGTAATCAT | AGCCATCGCC | 180 |
| CGCACGCCGA | GACTACAGAC | CATAACCAAC | GTGTTCGTGA | CTTCACTGGC | CGCAGCTGAC | 240 |
| TTGGTAGTGG | GACTCCTCGT | AATGCCACCA | GGGGCCACAT | GGCGCTGAC | TGGCCATTGG | 300 |
| CCCTTGGGCG | AAACTGGTTG | CGAACTGTGG | ACGTCAGTGG | ACGTGCTCTG | TGTAACTGCT | 360 |
| AGCATCGAGA | CCTTGTGCGC | CCTGGCTGTG | GACCGCTACC | TAGCTGTCAC | CAACCCTTTG | 420 |
| CGTTACGGCA | CGCTGGTTAC | CAAGCGCCGC | GCCCGCGCGG | CAGTTGTCCT | GGTGTGGATC | 480 |
| GTGTCCGCTG | CCGTGTCCTT | TGCGCCCATC | ATGAGCCAGT | GGTGGCGTGT | AGGGGCAGAT | 540 |
| GCCGAGGCAC | AGGAATGCCA | CTCCAATCCG | CGCTGCTGTT | CCTTTGCCTC | CAACATGCCC | 600 |
| TATGCGCTGC | TCTCCTCCTC | CGTCTCCTTC | TACCTTCCCC | TCCTTGTGAT | GCTCTTCGTC | 660 |
| TATGCTCGAG | TGTTCGTTGT | GGCTAAGCGC | CAACGGCATT | GCTGCGCCG | GGAACTGGGC | 720 |
| CGCTTCTCGC | CCGAGGAGTC | TCCGCCGTCT | CCGTCGCGCT | CTCCGTCCCC | TGCCACAGGC | 780 |
| GGGACACCCG | CGGCACCGGA | TGGAGTGCCC | CCTGCGGCC | GGCGGCCTGC | GCGCCTCCTG | 840 |
| CCACTCCGGG | AACACCGCGC | CCTGCGCACC | TTAGGTCTCA | TTATGGGCAT | CTTCTCTCTG | 900 |
| TGCTGGCTGC | CCTTCTTCCT | GGCCAACGTG | CTGCGCGCAC | TCGCGGGGCC | CTCTCTAGTT | 960 |
| CCCAGCGGAG | TTTTCATCGC | CCTGAACTGG | CTGGGCTATG | CCAACTCCGC | CTTCAACCCG | 1020 |
| GTCATCTACT | GCCGCAGCCC | GGACTTTCGC | GACGCCTTCC | GTCGTCTTCT | GTGTAGCTAC | 1080 |
| GGTGGCCGTG | GACCGGAGGA | GCCACGCGCA | GTCACCTTCC | CAGCCAGCCC | TGTTGAAGCC | 1140 |
| AGGCAGAGTC | CACCGCTCAA | CAGG | | | | 1164 |

(2) INFORMATION FOR SEQ ID NO:4:

(i) SEQUENCE CHARACTERISTICS:
(A) LENGTH: 1360 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

| | | | | | | |
|---|---|---|---|---|---|---|
| GGCGCCACAC | GAGATGGCTC | CGTGGCCTCA | CAGAAACGGC | TCTCTGGCTT | TGTGGTCGGA | 60 |
| CGCCCCTACC | CTGGACCCCA | GTGCAGCCAA | CACCAGTGGG | TTGCCAGGAG | TACCATGGGC | 120 |
| AGCGGCATTG | GCTGGGGCAT | TGCTGGCGCT | GGCCACGGTG | GGAGGCAACC | TGCTGGTAAT | 180 |
| CATAGCCATC | GCCCGCACGC | CGAGACTACA | GACCATAACC | AACGTGTTCG | TGACTTCACT | 240 |
| GGCCGCAGCT | GACTTGGTAG | TGGGACTCCT | CGTAATGCCA | CCAGGGGCCA | CATGGCGCT | 300 |
| GACTGGCCAT | TGGCCCTTGG | GCGAAACTGG | TTGCGAACTG | TGGACGTCAG | TGGACGTGCT | 360 |
| CTGTGTAACT | GCTAGCATCG | AGACCTTGTG | CGCCCTGGCT | GTGGACCGCT | ACCTAGCTGT | 420 |
| CACCAACCCT | TTGCGTTACG | GCACGCTGGT | TACCAAGCGC | CGCGCCCGCG | CGGCAGTTGT | 480 |
| CCTGGTGTGG | ATCGTGTCCG | CTGCCGTGTC | CTTTGCGCCC | ATCATGAGCC | AGTGGTGGCG | 540 |
| TGTAGGGGCA | GATGCCGAGG | CACAGGAATG | CCACTCCAAT | CCGCGCTGCT | GTTCCTTTGC | 600 |

```
CTCCAACATG CCCTATGCGC TGCTCTCCTC CTCCGTCTCC TTCTACCTTC CCCTCCTTGT        660
GATGCTCTTC GTCTATGCTC GAGTGTTCGT TGTGGCTAAG CGCCAACGGC ATTTGCTGCG        720
CCGGGAACTG GGCCGCTTCT CGCCCGAGGA GTCTCCGCCG TCTCCGTCGC GCTCTCCGTC        780
CCCTGCCACA GGCGGGACAC CCGCGGCACC GGATGGAGTG CCCCCCTGCG GCCGGCGGCC        840
TGCGCGCCTC CTGCCACTCC GGGAACACCG CGCCCTGCGC ACCTTAGGTC TCATTATGGG        900
CATCTTCTCT CTGTGCTGGC TGCCCTTCTT CCTGGCCAAC GTGCTGCGCG CACTCGCGGG        960
GCCCTCTCTA GTTCCCAGCG GAGTTTTCAT CGCCCTGAAC TGGCTGGGCT ATGCCAACTC       1020
CGCCTTCAAC CCGGTCATCT ACTGCCGCAG CCCGGACTTT CGCGACGCCT TCCGTCGTCT       1080
TCTGTGTAGC TACGGTGGCC GTGGACCGGA GGAGCCACGC GCAGTCACCT TCCCAGCCAG       1140
CCCTGTTGAA GCCAGGCAGA GTCCACCGCT CAACAGGTAG GGGACACGAG CGGGGACCG        1200
GAGTCTCTGG GTGGGACGT CTCTGTCTCT ATTTTGAGT TGGAGATTG GGGAGGGGA          1260
AGATGTAGAT GGGGTGCGG TGTGTGTG GGTGGGGGT GGCCTTTGTC TTGAGAGGAC         1320
AGAAAAGAGG TAGGAACTAA AACGGCCCT TTCTCTTCTT                              1360
```

( 2 ) INFORMATION FOR SEQ ID NO:5:

( i ) SEQUENCE CHARACTERISTICS:
( A ) LENGTH: 281 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

```
GTAGCTACGG TGGCCGTGGA CCGGAGGAGC CACGCGCAGT CACCTTCCCA GCCAGCCCTG         60
TTGAAGCCAG GCAGAGTCCA CCGCTCAACA GGTAGGGGAC ACGAGCGGGG GACCGGAGTC       120
TCTGGGTGGG GACGTCTCTG TCTCTATTTT TGAGTTTGGA GATTGGGGA GGGGAAGATG        180
TAGATGGGGG TGCGGTGTGT GTGTGGGTGG GGGTGGCCT TTGTCTTGAG AGGACAGAAA        240
AGAGGTAGGA ACTAAAACGG GCCCTTTCTC TTCTTGGATC C                           281
```

( 2 ) INFORMATION FOR SEQ ID NO:6:

( i ) SEQUENCE CHARACTERISTICS:
( A ) LENGTH: 609 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

```
TGGACGTCAG TGGACGTGCT CTGTGTAACT GCTAGCATCG AGACCTTGTG CGCCCTGGCT         60
GTGGACCGCT ACCTAGCTGT CACCAACCCT TTGCGTTACG GCACGCTGGT TACCAAGCGC       120
CGCGCCCGCG CGGCAGTTGT CCTGGTGTGG ATCGTGTCCG CTGCCGTGTC CTTTGCGCCC       180
ATCATGAGCC AGTGGTGGCG TGTAGGGGCA GATGCCGAGG CACAGGAATG CCACTCCAAT       240
CCGCGCTGCT GTTCCTTTGC CTCCAACATG CCCTATGCGC TGCTCTCCTC CTCCGTCTCC       300
TTCTACCTTC CCTCCTTGT GATGCTCTTC GTCTATGCTC GAGTGTTCGT TGTGGCTAAG       360
CGCCAACGGC ATTTGCTGCG CCGGGAACTG GGCCGCTTCT CGCCCGAGGA GTCTCCGCCG       420
TCTCCGTCGC GCTCTCCGTC CCCTGCCACA GGCGGGACAC CCGCGGCACC GGATGGAGTG       480
CCCCCCTGCG GCCGGCGGCC TGCGCGCCTC CTGCCACTCC GGGAACACCG CGCCCTGCGC       540
```

```
ACCTTAGGTC TCATTATGGG CATCTTCTCT CTGTGCTGGC TGCCCTTCTT CCTGGCCAAC         600

GTGCTGCGC                                                                609
```

( 2 ) INFORMATION FOR SEQ ID NO:7:

( i ) SEQUENCE CHARACTERISTICS:
        ( A ) LENGTH: 298 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GATGGCTCCG TGGCCTCACA GAAACGGCTC TCTGGCTTTG TGGTCGGACG CCCCTACCCT          60

GGACCCCAGT GCAGCCAACA CCAGTGGGTT GCCAGGAGTA CCATGGGCAG CGGCATTGGC         120

TGGGGCATTG CTGGCGCTGG CCACGGTGGG AGGCAACCTG CTGGTAATCA TAGCCATCGC         180

CCGCACGCCG AGACTACAGA CCATAACCAA CGTGTTCGTG ACTTCACTGG CCGCAGCTGA         240

CTTGGTAGTG GGACTCCTCG TAATGCCACC AGGGGCCACA TTGGCGCTGA CTGGCCAT          298
```

( 2 ) INFORMATION FOR SEQ ID NO:8:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Ala Ala Ala Leu Ala Gly Ala Leu Leu Ala Leu Ala Thr Val Gly Gly
 1               5                   10                  15

Asn Leu Leu Val Ile Ile Ala Ile Ala
                20              25
```

( 2 ) INFORMATION FOR SEQ ID NO:9:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Ser Tyr Gly Gly Arg Gly Pro Glu Glu Pro Arg Ala Val Thr Phe Pro
 1               5                   10                  15

Ala Ser Pro Val Glu Ala Arg Gln Ser Pro Pro Leu Asn Arg
                20              25                  30
```

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
AAGCTTGTCG TGCACGCGGC CAGCATCTGA GAACCCTGTG                               40
```

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | |
|---|---|---|---|
| GTCGACAAGA | AGGGCAGCAC | AGCAGAGGCA | GTGAA | 35 |

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GCATGCTCCG TGGCCTCACG AGAA         24

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CTGCAGGAGG AGGACAGCAG CA         22

( 2 ) INFORMATION FOR SEQ ID NO:14:

( i ) SEQUENCE CHARACTERISTICS:
        ( A ) LENGTH: 1134 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

| | | | | | |
|---|---|---|---|---|---|
| ATGGCTCCGT | GGCCTCACGA | GAACAGCTCT | CTTGCCCCAT | GGCCGGACCT | CCCCACCCTG | 60 |
| GCGCCCAATA | CCGCCAACAC | CAGTGGGCTG | CCAGGGGTTC | CGTGGGAGGC | GGCCCTAGCC | 120 |
| GGGCCCTGC | TGGCGCTGGC | GGTGCTGGCC | ACCGTGGGAG | GCAACCTGCT | GGTCATCGTG | 180 |
| GCCATCGCCT | GGACTCCGAG | ACTCCAGACC | ATGACCAACG | TGTTCGTGAC | TTCGCTGGCC | 240 |
| GCAGCCGACC | TGGTGATGGG | ACTCCTGGTG | GTGCCGCCGG | CGGCCACCTT | GCGCTGACT | 300 |
| GGCCACTGGC | CGTTGGGCGC | CACTGGCTGC | GAGCTGTGGA | CCTCGGTGGA | CGTGCTGTGT | 360 |
| GTGACCGCCA | GCATCGAAAC | CCTGTGCGCC | CTGGCCGTGG | ACCGCTACCT | GGCTGTGACC | 420 |
| AACCCGCTGC | GTTACGGCGC | ACTGGTCACC | AAGCGCTGCG | CCCGGACAGC | TGTGGTCCTG | 480 |
| GTGTGGGTCG | TGTCGGCCGC | GGTGTCGTTT | GCGCCCATCA | TGAGCCAGTG | GTGGCGCGTA | 540 |
| GGGGCCGACG | CCGAGGCGCA | GCGCTGCCAC | TCCAACCCGC | GCTGCTGTGC | CTTCGCCTCC | 600 |
| AACATGCCCT | ACGTGCTGCT | GTCCTCCTCC | GTCTCCTTCT | ACCTTCCTCT | TCTCGTGATG | 660 |

```
CTCTTCGTCT ACGCGCGGGT TTTCGTGGTG GCTACGCGCC AGCTGCGCTT GCTGCGCGGG      720

GAGCTGGGCC GCTTTCCGCC CGAGGAGTCT CCGCCGGCGC CGTCGCGCTC TCTGGCCCCG      780

GCCCCGGTGG GGACGTGCGC TCCGCCCGAA GGGGTGCCCG CCTGCGGCCG GCGGCCCGCG      840

CGCCTCCTGC CTCTCCGGGA CACCGGGCC  CTGTGCACCT TGGGTCTCAT CATGGGCACC      900

TTCACTCTCT GCTGGTTGCC CTTCTTTCTG GCCAACGTGC TGCGCGCCCT GGGGGGCCCC      960

TCTCTAGTCC CGGGCCCGGC TTTCCTTGCC CTGAACTGGC TAGGTTATGC CAATTCTGCC     1020

TTCAACCCGC TCATCTACTG CCGCAGCCCG GACTTTCGCA GCGCCTTCCG CCGTCTTCTG     1080

TGCCGCTGCG GCCGTCGCCT GCCTCCGGAG CCCTGCGCCG CCGCCCGCCC GGCC           1134
```

( 2 ) INFORMATION FOR SEQ ID NO:15:

( i ) SEQUENCE CHARACTERISTICS:
        ( A ) LENGTH: 402 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Met Ala Pro Trp Pro His Glu Asn Ser Ser Leu Ala Pro Trp Pro Asp
 1               5                  10                  15

Leu Pro Thr Leu Ala Pro Asn Thr Ala Asn Thr Ser Gly Leu Pro Gly
                20                  25                  30

Val Pro Trp Glu Ala Ala Leu Ala Gly Ala Leu Leu Ala Leu Ala Val
            35                  40                  45

Leu Ala Thr Val Gly Gly Asn Leu Leu Val Ile Val Ala Ile Ala Trp
    50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
            100                 105                 110

Trp Thr Ser Val Asp Val Leu Cys Val Thr Ala Ser Ile Glu Thr Leu
    115                 120                 125

Cys Ala Leu Ala Val Asp Arg Tyr Leu Ala Val Thr Asn Pro Leu Arg
130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
    195                 200                 205

Ser Ser Val Ser Phe Tyr Leu Pro Leu Leu Val Met Leu Phe Val Tyr
210                 215                 220

Ala Arg Val Phe Val Val Ala Thr Arg Gln Leu Arg Leu Leu Arg Gly
225                 230                 235                 240

Glu Leu Gly Arg Phe Pro Pro Glu Glu Ser Pro Pro Ala Pro Ser Arg
                245                 250                 255

Ser Leu Ala Pro Ala Pro Val Gly Thr Cys Ala Pro Pro Glu Gly Val
            260                 265                 270
```

```
Pro  Ala  Cys  Gly  Arg  Arg  Pro  Ala  Arg  Leu  Leu  Pro  Leu  Arg  Glu  His
          275                      280                      285

Arg  Ala  Leu  Cys  Thr  Leu  Gly  Leu  Ile  Met  Gly  Thr  Phe  Thr  Leu  Cys
     290                      295                      300

Trp  Leu  Pro  Phe  Phe  Leu  Ala  Asn  Val  Leu  Arg  Ala  Leu  Gly  Gly  Pro
305                      310                      315                      320

Ser  Leu  Val  Pro  Gly  Pro  Ala  Phe  Leu  Ala  Leu  Asn  Trp  Leu  Gly  Tyr
               325                      330                      335

Ala  Asn  Ser  Ala  Phe  Asn  Pro  Leu  Ile  Tyr  Cys  Arg  Ser  Pro  Asp  Phe
               340                      345                      350

Arg  Ser  Ala  Phe  Arg  Arg  Leu  Leu  Cys  Arg  Cys  Gly  Arg  Arg  Leu  Pro
          355                      360                      365

Pro  Glu  Pro  Cys  Ala  Ala  Ala  Arg  Pro  Ala  Leu  Phe  Pro  Ser  Gly  Val
     370                      375                      380

Pro  Ala  Ala  Arg  Ser  Ser  Pro  Ala  Gln  Pro  Arg  Leu  Cys  Gln  Arg  Leu
385                      390                      395                      400

Asp  Gly
```

( 2 ) INFORMATION FOR SEQ ID NO:16:

( i ) SEQUENCE CHARACTERISTICS:
        ( A ) LENGTH: 477 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Met  Gly  Ala  Gly  Val  Leu  Val  Leu  Gly  Ala  Ser  Glu  Pro  Gly  Asn  Leu
1                   5                        10                       15

Ser  Ser  Ala  Ala  Pro  Leu  Pro  Asp  Gly  Ala  Ala  Thr  Ala  Ala  Arg  Leu
               20                       25                       30

Leu  Val  Pro  Ala  Ser  Pro  Pro  Ala  Ser  Leu  Leu  Pro  Pro  Ala  Ser  Glu
               35                       40                       45

Ser  Pro  Glu  Pro  Leu  Ser  Gln  Gln  Trp  Thr  Ala  Gly  Met  Gly  Leu  Leu
     50                       55                       60

Met  Ala  Leu  Ile  Val  Leu  Leu  Ile  Val  Ala  Gly  Asn  Val  Leu  Val  Ile
65                       70                       75                       80

Val  Ala  Ile  Ala  Lys  Thr  Pro  Arg  Leu  Gln  Thr  Leu  Thr  Asn  Leu  Phe
               85                       90                       95

Ile  Met  Ser  Leu  Ala  Ser  Ala  Asp  Leu  Val  Met  Gly  Leu  Leu  Val  Val
               100                      105                      110

Pro  Phe  Gly  Ala  Thr  Ile  Val  Val  Trp  Gly  Arg  Trp  Glu  Tyr  Gly  Ser
          115                      120                      125

Phe  Phe  Cys  Glu  Leu  Trp  Thr  Ser  Val  Asp  Val  Leu  Cys  Val  Thr  Ala
     130                      135                      140

Ser  Ile  Glu  Thr  Leu  Cys  Val  Ile  Ala  Leu  Asp  Arg  Tyr  Leu  Ala  Ile
145                      150                      155                      160

Thr  Ser  Pro  Phe  Arg  Tyr  Gln  Ser  Leu  Leu  Thr  Arg  Ala  Arg  Ala  Arg
               165                      170                      175

Gly  Leu  Val  Cys  Thr  Val  Trp  Ala  Ile  Ser  Ala  Leu  Val  Ser  Phe  Leu
               180                      185                      190

Pro  Ile  Leu  Met  His  Trp  Trp  Arg  Ala  Glu  Ser  Asp  Glu  Ala  Arg  Arg
          195                      200                      205

Cys  Tyr  Asn  Asp  Pro  Lys  Cys  Cys  Asp  Phe  Val  Thr  Asn  Arg  Ala  Tyr
```

-continued

```
              210                           215                           220
Ala  Ile  Ala  Ser  Ser  Val  Val  Ser  Phe  Tyr  Val  Pro  Leu  Cys  Ile  Met
225                      230                      235                          240
Ala  Phe  Val  Tyr  Leu  Arg  Val  Phe  Arg  Glu  Ala  Gln  Lys  Gln  Val  Lys
                    245                      250                      255
Lys  Ile  Asp  Ser  Cys  Glu  Arg  Arg  Phe  Leu  Gly  Gly  Pro  Ala  Arg  Pro
                260                      265                      270
Pro  Ser  Pro  Ser  Pro  Ser  Pro  Val  Pro  Ala  Pro  Ala  Pro  Pro  Pro  Gly
          275                      280                      285
Pro  Pro  Arg  Pro  Ala  Ala  Ala  Ala  Thr  Ala  Pro  Leu  Ala  Asn  Gly
     290                      295                      300
Arg  Ala  Gly  Lys  Arg  Arg  Pro  Ser  Arg  Leu  Val  Ala  Leu  Arg  Glu  Gln
305                      310                      315                          320
Lys  Ala  Leu  Lys  Thr  Leu  Gly  Ile  Ile  Met  Gly  Val  Phe  Thr  Leu  Cys
                    325                      330                      335
Trp  Leu  Pro  Phe  Phe  Leu  Ala  Asn  Val  Val  Lys  Ala  Phe  His  Arg  Glu
                340                      345                      350
Leu  Val  Pro  Asp  Arg  Leu  Phe  Val  Phe  Phe  Asn  Trp  Leu  Gly  Tyr  Ala
               355                      360                      365
Asn  Ser  Ala  Phe  Asn  Pro  Ile  Ile  Tyr  Cys  Arg  Ser  Pro  Asp  Phe  Arg
     370                      375                      380
Lys  Ala  Phe  Gln  Gly  Leu  Leu  Cys  Cys  Ala  Arg  Arg  Ala  Ala  Arg  Arg
385                      390                      395                          400
Arg  His  Ala  Thr  His  Gly  Asp  Arg  Pro  Arg  Ala  Ser  Gly  Cys  Leu  Ala
               405                      410                      415
Arg  Pro  Gly  Pro  Pro  Ser  Pro  Gly  Ala  Ala  Ser  Asp  Asp  Asp  Asp
               420                      425                      430
Asp  Asp  Val  Val  Gly  Ala  Thr  Pro  Ala  Arg  Leu  Leu  Glu  Pro  Trp
          435                      440                      445
Ala  Gly  Cys  Asn  Gly  Gly  Ala  Ala  Ala  Asp  Ser  Asp  Ser  Ser  Leu  Asp
     450                      455                      460
Glu  Pro  Cys  Arg  Pro  Gly  Phe  Ala  Ser  Glu  Ser  Lys  Val
465                      470                      475
```

( 2 ) INFORMATION FOR SEQ ID NO:17:

( i ) SEQUENCE CHARACTERISTICS:
        ( A ) LENGTH: 413 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Met  Gly  Gln  Pro  Gly  Asn  Gly  Ser  Ala  Phe  Leu  Leu  Ala  Pro  Asn  Gly
1                   5                        10                       15
Ser  His  Ala  Pro  Asp  His  Asp  Val  Thr  Gln  Gln  Arg  Asp  Glu  Val  Trp
               20                       25                       30
Val  Val  Leu  Met  Gly  Ile  Val  Met  Ser  Leu  Ile  Val  Leu  Ala  Ile  Val
               35                       40                       45
Phe  Gly  Asn  Val  Leu  Val  Ile  Thr  Ala  Ile  Ala  Lys  Phe  Glu  Arg  Leu
     50                       55                       60
Gln  Thr  Val  Thr  Asn  Tyr  Phe  Ile  Thr  Ser  Leu  Ala  Cys  Ala  Asp  Leu
65                       70                       75                            80
Val  Met  Gly  Leu  Ala  Val  Val  Pro  Phe  Gly  Ala  Ala  His  Ile  Leu  Met
               85                       90                       95
```

|   |   |   |   |   |   |   |   |   |   |   |   |   |   |   |
|---|---|---|---|---|---|---|---|---|---|---|---|---|---|---|
| Lys | Met | Trp | Thr 100 | Phe | Gly | Asn | Phe | Trp 105 | Cys | Glu | Phe | Trp | Thr 110 | Ser | Ile |
| Asp | Val | Leu 115 | Cys | Val | Thr | Ala | Ser 120 | Ile | Glu | Thr | Leu | Cys 125 | Val | Ile | Ala |
| Val | Asp 130 | Arg | Tyr | Phe | Ala | Ile 135 | Thr | Ser | Pro | Phe | Lys 140 | Tyr | Gln | Ser | Leu |
| Leu 145 | Thr | Arg | Asn | Lys | Ala 150 | Arg | Val | Ile | Ile | Leu 155 | Met | Val | Trp | Ile | Val 160 |
| Ser | Gly | Leu | Thr | Ser 165 | Phe | Leu | Pro | Ile | Gln 170 | Met | His | Trp | Tyr | Arg 175 | Ala |
| Thr | His | Gln | Glu 180 | Ala | Ile | Asn | Cys | Tyr 185 | Ala | Asn | Glu | Thr | Cys 190 | Cys | Asp |
| Phe | Phe | Thr 195 | Asn | Gln | Ala | Tyr | Ala 200 | Ile | Ala | Ser | Ser | Ile 205 | Val | Ser | Phe |
| Tyr | Val 210 | Pro | Leu | Val | Ile | Met 215 | Val | Phe | Val | Tyr | Ser 220 | Arg | Val | Phe | Gln |
| Glu 225 | Ala | Lys | Arg | Gln | Leu 230 | Gln | Lys | Ile | Asp | Lys 235 | Ser | Glu | Gly | Arg | Phe 240 |
| His | Val | Gln | Asn | Leu 245 | Ser | Gln | Val | Glu | Gln 250 | Asp | Gly | Arg | Thr | Gly 255 | His |
| Gly | Leu | Arg | Arg 260 | Ser | Ser | Lys | Phe | Cys 265 | Leu | Lys | Glu | His | Lys 270 | Ala | Leu |
| Lys | Thr | Leu 275 | Gly | Ile | Ile | Met | Gly 280 | Thr | Phe | Thr | Leu | Cys 285 | Trp | Leu | Pro |
| Phe | Phe 290 | Ile | Val | Asn | Ile | Val 295 | His | Val | Ile | Gln | Asp 300 | Asn | Leu | Ile | Arg |
| Lys 305 | Glu | Val | Tyr | Ile | Leu 310 | Leu | Asn | Trp | Ile | Gly 315 | Tyr | Val | Asn | Ser | Gly 320 |
| Phe | Asn | Pro | Leu | Ile 325 | Tyr | Cys | Arg | Ser | Pro 330 | Asp | Phe | Arg | Ile | Ala 335 | Phe |
| Gln | Glu | Leu | Leu 340 | Cys | Leu | Arg | Arg | Ser 345 | Ser | Leu | Lys | Ala | Tyr 350 | Gly | Asn |
| Gly | Tyr | Ser 355 | Ser | Asn | Gly | Asn | Thr 360 | Gly | Glu | Gln | Ser | Gly 365 | Tyr | His | Val |
| Glu | Gln 370 | Glu | Lys | Glu | Asn | Lys 375 | Leu | Leu | Cys | Glu | Asp 380 | Leu | Pro | Gly | Thr |
| Glu 385 | Asp | Phe | Val | Gly | His 390 | Gln | Gly | Thr | Val | Pro 395 | Ser | Asp | Asn | Ile | Asp 400 |
| Ser | Gln | Gly | Arg | Asn 405 | Cys | Ser | Thr | Asn | Asp 410 | Ser | Leu | Leu |  |  |  |